United States Patent
Peles

(10) Patent No.: US 8,083,694 B2
(45) Date of Patent: *Dec. 27, 2011

(54) MULTI JOINT ORTHODYNAMIC REHABILITATOR, ASSISTIVE ORTHOTIC DEVICE AND METHODS FOR ACTUATION CONTROLLING

(75) Inventor: Zalman Peles, M. P. Corazim (IL)

(73) Assignee: Muscle Tech Ltd. (IL)

( * ) Notice: Subject to any disclaimer, the term of this patent is extended or adjusted under 35 U.S.C. 154(b) by 1231 days.

This patent is subject to a terminal disclaimer.

(21) Appl. No.: 11/783,625

(22) Filed: Apr. 11, 2007

(65) Prior Publication Data

US 2008/0077057 A1    Mar. 27, 2008

Related U.S. Application Data

(63) Continuation-in-part of application No. 10/446,808, filed on May 29, 2003, now Pat. No. 7,204,814.

(51) Int. Cl.
*A61H 1/00* (2006.01)

(52) U.S. Cl. ............................................. 601/5; 601/33

(58) Field of Classification Search ................ 601/5, 23, 601/3, 34, 35, 40; 602/16, 20, 21
See application file for complete search history.

(56) References Cited

U.S. PATENT DOCUMENTS

| | | |
|---|---|---|
| 4,558,692 A | 12/1985 | Greiner |
| 4,601,468 A | 7/1986 | Bond et al. |
| 4,697,808 A | 10/1987 | Larson et al. |
| 4,711,450 A | 12/1987 | McArthur |
| 4,828,257 A | 5/1989 | Dyer et al. |
| 4,885,939 A | 12/1989 | Martin |
| 5,078,152 A | 1/1992 | Bond et al. |
| 5,121,747 A | 6/1992 | Andrews |
| 5,211,161 A | 5/1993 | Stef |
| 5,252,102 A | 10/1993 | Singer et al. |
| 5,399,147 A | 3/1995 | Kaiser |
| 5,466,213 A | 11/1995 | Hogan et al. |
| 5,662,693 A | 9/1997 | Johnson et al. |
| 5,961,541 A | 10/1999 | Ferrati |
| 6,035,274 A | 3/2000 | Kramer et al. |
| 6,109,852 A | 8/2000 | Shahinpoor et al. |
| 6,221,032 B1 | 4/2001 | Blanchard et al. |
| 6,244,873 B1 | 6/2001 | Hill et al. |
| 6,267,735 B1 | 7/2001 | Blanchard et al. |
| 6,379,393 B1 | 4/2002 | Mavroidis et al. |
| 6,450,922 B1 | 9/2002 | Henderson et al. |
| 7,204,814 B2 * | 4/2007 | Peles ................. 601/5 |
| 2004/0102723 A1 | 5/2004 | Horst |

OTHER PUBLICATIONS

Optiflex S—User Manual (Chattanooga Group Inc) Medtrade 2002.
http://www.asel.udel.edu/robotics/newsletter/showcase12.html, Jan. 15, 1998.
http://www.asel.udel.edu/ robotics/newsletter/showcase12.html, Jan. 15, 1998.

* cited by examiner

*Primary Examiner* — Quang D Thanh
(74) *Attorney, Agent, or Firm* — Bacon & Thomas, PLLC

(57) ABSTRACT

A method and system for treating self-adaptive motion of a jointed body part of a patient, the jointed body part has at least three rotatable body sections interconnected by at least two joints, by collecting data regarding limb movement displaying representations of the data in real time, and modifying current device function based upon such data so as to meet predefined therapeutic treatment parameters with regard to device-actuated movement needs of the limb regarding device-actuated movement, and/or assist limb rotation.

14 Claims, 33 Drawing Sheets

Orthesis main axis rotation 0 - 135°

Open Arm Position

Folded 20°

Folded 90°

Folded 135°

|  | | 252 | 250 | 256 | 258 |
|---|---|---|---|---|---|
|  | Elbow | Position | Max force | 0.5 Scale |
|  |  | Inner | | |
|  |  | Middle | | |
|  |  | Outer | | |
| 254 | Forearm | Position | Max force | 0.5 Scale |
|  |  | Inner | | |
|  |  | Middle | | |
|  |  | Outer | | |

*Figure 19*

MULTI JOINT ORTHODYNAMIC REHABILITATOR, ASSISTIVE ORTHOTIC DEVICE AND METHODS FOR ACTUATION CONTROLLING

CROSS-REFERENCE TO RELATED APPLICATION

This application is a continuation-in-part of U.S. application Ser. No. 10/446,808 filed on 29 May 2003, to issue as U.S. Pat. No. 7,204,814, entitled "Orthodynamic Rehabilitator".

FIELD OF THE INVENTION

The present invention relates to a multi joint orthodynamic rehabilitator, assistive orthotic device and methods for actuation controlling

BACKGROUND OF THE INVENTION

It is known in the field of rehabilitative medicine that providing range of motion to partially and/or fully non-functional limbs prevents muscle atrophy. Range of motion exercises after surgery is known to decrease post-operative pain and swelling.

Historically, movement of the limb was provided "hands on" by a therapist. In recent years, however, the hands of the therapists are being replaced by rehabilitative orthotic devices, the most popular currently appears to be the group on devices referred to as "continuous passive motion" (CPM) machines. While the CPMs relieve the therapist from the mundane job of moving a limb repeatedly through a prescribed range of motion, the machines lack the human hands-on feel of the nuances of how the limb's response to the movement. The lack of sensitivity of the part of CPM machines also creates a situation wherein the limb may be even further damaged by the continuation of movement if an emergency, such as resistance to the movement, occurs. The challenge has become finding ways for machines to collect and implement data with similar results to the "hands-on" data collected implemented mentally by a therapist.

A number of CPM devices have been developed that use resistance to the movement of the device to trigger a modification of the devices movement. These modifications, however, are based only attaining a preset threshold of resistance to movement, and are generally stopping or reversing direction of the actuating member of the device, or a combination of the two. U.S. Pat. No. 4,558,692 to Greiner describes a device that includes an override switch that, if resistance is encountered, will automatically stop and reverse the motor to prevent injury or discomfort to the patient. The Optiflex™, marketed by Chattanooga Group, Inc., utilizes a similar safety feature.

Another attempt to humanize CPM devices is disclosed in U.S. Pat. No. 6,267,735 to Blanchard et al. The Blanchard et al. device is a continuous passive motion device that may be programmed to stop and reverse the direction of its carriage when a patient activates a "Comfort Zone" feature upon experiencing discomfort during flexion or extension. The device may be programmed to establish a reduced range of motion or Comfort Zone for a number of cycles of flexion and extension, after which the range of motion will preferably be gradually and automatically increased or advanced until flexion and/or extension may be carried out at the point at which discomfort was experienced. The preferred embodiment of the Blanchard et al. device thus provides the patient with immediate relief from discomfort while allowing flexion and extension to continue automatically and in a controlled manner until flexion and/or extension may be carried out at the point at which discomfort was experienced. In this way, the preferred embodiment of the Blanchard et al. device provides a CPM device which may be operated so as to decrease the likelihood that the patient will experience similar discomfort when the carriage returns to the point along the axis of the frame at which discomfort was initially experienced (and at which the Comfort Zone feature was actuated). The human element, however, is just that, and while the Blanchard et al. device allows a wider range of human input to the operational parameters of the machine, it does not provide information relating to the bodies response to therapy other than discomfort zones.

The above referenced CPM machines are characterized as being for therapeutic rehabilitation use. The Motorized Upper Limb Orthotic System (MULOS) developed by the Centre for Rehabilitation and Engineering Studies (CREST), University of Newcastle upon Tyne, UK, is a device that can operate in a CPM mode or an assistive mode. In its assistive mode, the device is controlled by a joystick so as to direct the movement of the limb. The MULOS is also a very large device that is mounted on a wheelchair.

Another field of art pertinent to the present invention is that of iso-kinetic systems, such as those disclosed in U.S. Pat. No. 4,711,450 to McArthur, U.S. Pat. No. 4,885,939 to Martin, and U.S. Pat. No. 4,601,468 to Bond et al. These devices are generally large, non-portable, single function machines, and must be operated by trained professionals. Some of the devices in this category are able to adjust the level of resistance to movement as either more resistance or less resistance, however, their use is limited to diagnostic measurement of a single joint, and a different device is used for actual therapy sessions.

Other than emergency stop procedures, the data collection of the above referenced devices is limited to collection of data for use in subsequent therapeutic sessions. None of these devices is configured to collect data in real time for substantially immediate implementation.

There is therefore a need for a portable orthotic system that collects data regarding limb movement, displays representations of the data in real time, and modifies current device function based upon such data so as to meet predefined therapeutic treatment parameters with regard to device-actuated movement needs of the limb regarding device-actuated movement, and/or assist limb rotation range of motion and while doing so even amplify the patient's power to a level none dangerous to the patients. It would be of benefit if the system could be operated by a patient, at least during therapy sessions and when used as an assistive device. It would be of further benefit if the system could be used outside of a clinic, such as in a patient's home, with data communication to a clinic. It would be of benefit if the system could be operated by a user such as geriatric or even partially disabled patient that had already reached the limits of their rehabilitation and need farther assistance to perform at list their main every day living functions, such as: opening a door, dropping and wearing trousers, drinking from a cup and turning pages in a book.

SUMMARY OF THE INVENTION

The present invention is a portable exoskeleton multi-joint wear on orthotic system that collects data regarding limb movement, displays representations of the data in real time, and modifies current device function based upon such data so as to meet predefined therapeutic treatment parameters with regard to device-actuated movement needs of the limb regarding device-actuated movement, and/or assist limb rotation.

According to the teachings of the present invention there is provided, farther modification of the orthodynamic rehabilitator US patent application No. 20040243025 having innovative steps: The original patent preferred embodiment is basically a double jointed elbow device, designed to function as rehabilitator for elbow and wrist only. On clinic terms it is called "Elbow device". while the currant invention is a true multi-joint Orthosis of the upper limb; functioning with no less than three joint but the disclosed preferred embodiment has in effect 6 joints capable of working simultaneously on all joints while the upper limb unit as a whole operates on x, y, z axels in relation to the user's body.

The present invention adds at list an extra joint (e.g., a shoulder joint) that is adapted to grant the said orthosis with additional rehabilitating and assisting capabilities that a double joint apparatus can not perform. The use of a shoulder joint enables the whole arm to rotate at list horizontally and provided with an alternative mechanical shoulder "bowl and socket joint" it can also rotate the whole arm vertically, The use of the said two axis simultaneously enables the device to rotate also on its Z axis in a manner that the entire disclosed orthetic devise maneuvers on its x, y, z axis.

This rotation pattern allows the use of the orthodynamic rehabilitation program to rehabilitate and assist the upper limb to it full extent. In order to be able to perform in the said method; the device is capable of working in two modes—the rehabilitating active mode and the passive assisting mode. The work capabilities of the disclosed invention on the active and/or passive modes is enabled by the invented method of software programming aimed to allow a qualified therapist or to control the hardware components (each or all) by use of the inbuilt capacity of the said software programming. AS soon as the devise worn on the user's limb—the said program records the users impairness by assessing the parameters of: the user's active range of motion, passive range of motion, and power and records it in its memory, the said program using a processor constantly records changing data of the Orthotic user making the difference to be regarded in a manner of ordering a reaction of the device according to preset medical allowances and programmed treatments. The said invented device could be fit as an assistive tool by using only a part of the said program capacity to record and assess direction of motion and amount of power exerted by the user to perform the same motion—in order to react as an amplifier to increase the patients power by a measured amount, thus increase the patient capacity to perform every day living chores in a modified and useful manner.

The invented device innovative design allows the said hardware to function as exoskeleton multi-joint wear on orthotic system designed to function as rehabilitator and assistive device aimed to improve the quality of life of motion and power impaired users.

In order to achieve the said purpose and goals the said device composes harnessing parts, allowing the device to tie on the human body as an exoskeleton jointed members carrying farther hardware components such as computer controlled hydraulic and electric actuators, sensors designed to record the power, direction and angle of each joint. Processor mounted on an electronic M board designed to process and pass on electronic data coming from sensors and translate digital data coming from a computerized memory to electronic signs designed to control the actuators and their sub systems such as main hydraulics and electric power sour and relays that enables the said exoskeleton machine to manipulate the human limb that its tied on—according to its various joints and allowed capacity of movement and allowed power.

A wear on multi-joint exoskeleton device, comprising at least 3 joints and 3 actuators; attached on the human body and fitted particularly on the human limb designed to be used as robotic rehabilitation machine and/or assistive device for partially upper limb impaired patients—by use of hardware that includes computer controlled actuators, controlled by software and processor that via electronic board (M board) operates the device intelligently to perform the following needs and functions:

The disclosed multi-joint device designed and programmed for rehabilitation of neurologically impaired patience by relaying on its imbedded assistive capabilities, thus, it reacts on real time to the patient power by exerting the necessary forces.

Prior to the treatment the device assessing the impairers parameters of the patient limb by checking the active range of the patient's motions, and the passive range of the patient's motions, and the maximal power that the patient can exert at 'active range of motion' mode. The device records the said accumulated data and keeps it in its memory. The said data is sent at the therapist will to a printer, and/or, (by its inbuilt communication module) to a remote computer station to the clinic (telemedicine capabilities).

This device programmed to analyze and remember changing rehabilitation parameters (for example—the patient gets weaker during the last session of the treatment) on real time, and react with the proper force according to the patient changed position and power (artificial intelligence).

The device programmed to activate a neurological stimulus by its capability to react to the patience power (as limited as it may be) by exerting a properly measured counter force against the said patient's straining muscles and joints. Thus, it enables the patience proprioceptive system (that otherwise could not react to a motionless limb). Since most CVA patients has a partially destroyed motion aria (Cortex) in their brains—they will learn to create alternative rout to control the disabled limb through the part of the brain that is commending the proprioceptive system that was not effected by the said CVA event that had effected the said patient's motion center.

The additional functions such as telemedicine capabilities, extended neurological rehabilitation capabilities, and capabilities of a wear on assistive device that could be worn on an impaired upper limb as a sleeve. The said innovative functions technology operated only on a multi joint robotic device that has the hardware and software technical capabilities to manipulate and control three joints or more moving simultaneously on x, y, z axis, i.e., only by operating an exoskeleton with joints that are parallel by placing and functionality to the natural human body, for example the human upper limb has the fingers joints, wrist joint, elbow joint, shoulder joints; it is possible to rehabilitate or assist the full functioning of the most needed every day living functions (ADL) like opening a door, pick up a phone, turning pages in a book, eating and drinking, and dropping or lifting trousers when needed. This innovative functionality allows the design and construction of the said assistive devise that could be fully mobile and worn as a sleeve to assist geriatric and other partially impaired used to perform their ADL needs to better extant.

BRIEF DESCRIPTION OF THE DRAWINGS

The invention is herein described, by way of example only, with reference to the accompanying drawings, wherein:

FIG. 19 shows a table representation of data collected during classical muscle testing according to the teachings of the present invention;

FIGS. 28 to 33 illustrate the designed controlled rotation of the exoskeleton parts around the various axels of the multi joint orthosis wherein:

FIG. 28 shows parts (a) and (b) shows the rotation pattern (Pronation Supination) of the wrist ring and parts;

FIG. 29 shows parts (a) and (b) shows the rotation pattern of the forearm on the elbow axis (extension and flexion) operating and control pattern of the elbow sub system;

FIG. 30 shows parts (a) and (b) shows the design of the controlled rotation pattern of the arm around the lower shoulder extending axel causing the forearm and hand parts to rotate around the human body to the left and right as needed;

FIG 31 shows parts (a) and (b) which illustrate the design of the controlled rotation pattern of the arm and forearm around the main shoulder axis; and, FIG. 32 shows parts (a), (b) and (c) which illustrate the design of the controlled rotation pattern of the arm and forearm extended horizontally to the human body by rotating on the lower shoulder axel, and more so; the orthosis is allowed to be elevated vertically by rotation on the secondary shoulder plate axel for farther extension of the upper limb to reach maximum range of motion.

FIG. 33 shows part (a) and (b) which illustrate the design of the arm subsystem rotation around axis 45 when the same is continued. Namely when the arm reaches 90 degrees the joint locks and yet another shoulder joint 43 takes it functioning role and provide the arm with another extension of 45 degrees on the same plane to prolong the limb range of motion as much as possible within the natural limitation of the user.

DESCRIPTION OF THE PREFERRED EMBODIMENTS

Figure 1:
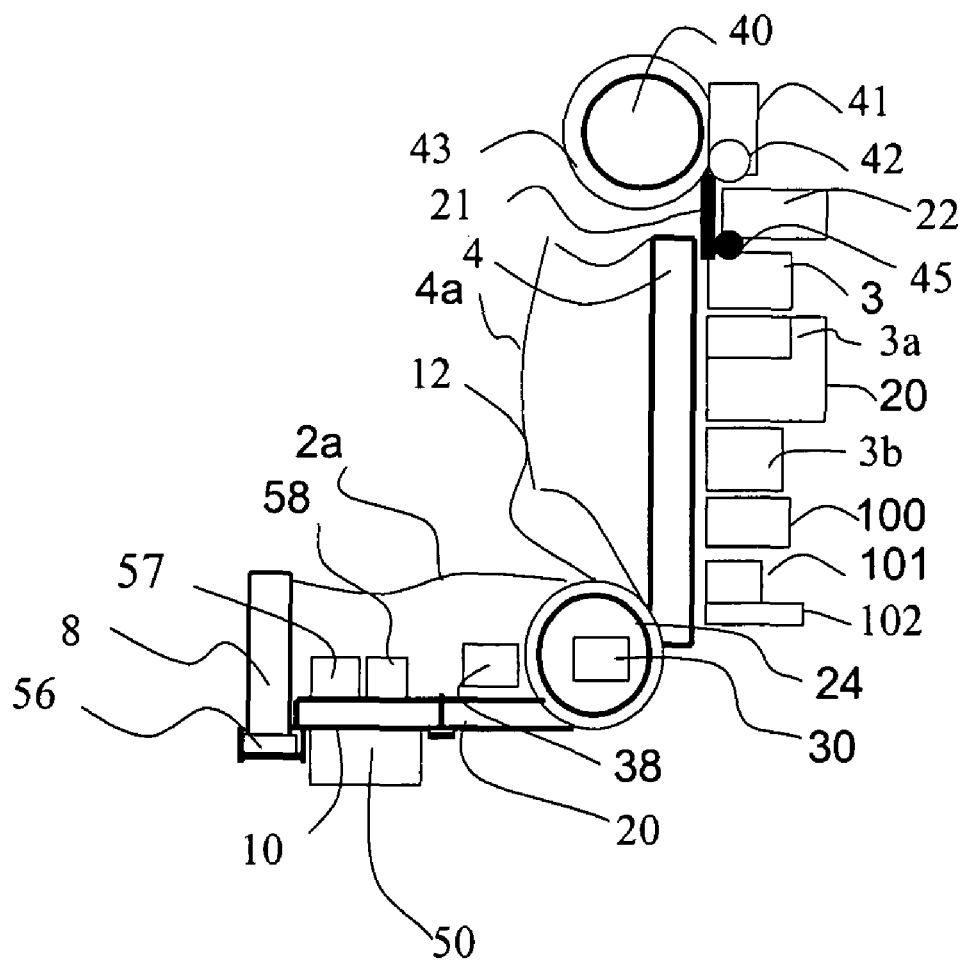
FIG. 1 is an out-of-scale schematic view of a multi-joint orthotic system composing subsystems constructed and operative according to the principles of the present invention.

The additional functions such as telemedicine capabilities, extended neurological rehabilitation The present invention is a portable orthotic system that collects data regarding limb movement, displays representations of the data in real time, and modifies current device function based upon such data so as to meet predefined therapeutic treatment parameters with regard to device-actuated movement needs of the limb regarding device-actuated movement, and/or assist limb rotation The device of the present invention is an exoskeleton rehabilitative assistive robot composed of 5 sub systems. The device sub systems relate to the various axes that enable its unique functions in the robot as follows:

Wrist subsystem composed of clipper grip axel and finger rods attached to the thumb and the finger proving the essential grip function for the user. The said clippers are mounted on the wrist ring and actuated by an actuator mounted on the said ring. The said ring is allowed to rotates 180 degrees on its forearm axis, by computer program controlled sensors and actuators located on the dorsal side of the forearm chassis.

The Elbow subsystem composed of the forearm chassis the Elbow joint and the Arm chassis. The said members are allowed to rotate 135 degrees on and around the said elbow axis, The said ring is allowed to rotates 180 degrees on its forearm axis, by computer program controlled sensors and actuators located on the dorsal side of the forearm chassis.

The elbow assembly is hung by the horizontal movement axel on the shoulder assembly in a way that allows the elbow assembly rotates horizontally on the said axel the said elbow assembly allowed to rotates 160 degrees on the said horizontal movement axel, by computer controlled program; sensors and an actuator located on the ventral side of the shoulder body. The elbow assembly is allowed to rotate around its said axels while rotating horizontally in respect to the human body.

The shoulder subsystem is a double jointed subsystem apparatus designed to substitute some of the essential function of the natural shoulder joint by allowing mechanical use of multiple axis that allows rotation of the entire upper limb on x, y, z dimensions.

The pad subsystem designed as harness for right and/or left limb. The principles and operation of an orthotic system according to the present invention may be better understood with reference to the drawings and the accompanying description.

By way of introduction, the non-limiting example of an orthotic system herein described relates to an orthesis for the elbow and forearm. It should be noted that the principles of the present invention may be applied to devices configured to rotate substantially any jointed body part, such as, but not limited to, the shoulder, the hip, the knee, and the spine. Further, the principles of the present invention need not be limited solely to devices for humans; therefore, veterinary devices are within the scope of the present invention.

A principle of the present invention is to collect and analyze data relating to the response of the patient to the movement of the external actuating device during a treatment session. The system then modifies at least one operational parameter of the system so as to optimize the rehabilitative process performed by the system. Prior art systems are known to change device functions so as to meet predefined operational parameters, such as constant velocity through a range of motion. The present invention by contrast, modifies the operational parameters so as to meet or maintain an optimal rehabilitative level. For example, iso-kinetic device of prior art will modify the amount of resistive force so as to maintain a predefined velocity. The system of the present invention will redefine the velocity parameter if the rehabilitative level falls outside of a predefined optimal range. The operational difference between the prior art systems and the system of the present invention is that each time the patient moves in the same way, the devices of prior art will make the response. The system of the present invention, however will determine if the movement of the patient falls outside of the optimal rehabilitative range, and if it does, will make a different response on successive occurrences of the movement.

Another principle of the present invention is the storage and retrieval of the patient related data from each assessment and/or treatment session. Such data may form a database, data from which may be used for long term analysis of, by non-limiting example, treatment effectiveness, rehabilitative progress monitoring, attainment of treatment benchmarks, and to aid in the decision making process of the treatment team. Data analysis may be in the form of, by non-limiting example, comparing the data sets resulting from previous sessions with the new acquired data from a current session while the session is in progress or at the termination of the session, or analysis of the full database to determine attainment of treatment or rehabilitative benchmarks. Such benchmarks may include, by non-limiting example, attainment of maximum rehabilitative level. This may be determined by attainment of predefined amount of limb use, such as full or 75% of lime use, or through data analysis showing a leveling off of rehabilitative progress, at which point, a percentage of limb use may be determined and a level of disability assigned.

Data supplied by the system may aid in the decision-making of the treatment team based on the progress monitoring, where the control program may suggest changes in the rehabilitation process based on rules defined by the physician/doctor or stored in the program as an expert knowledge database. Using these features, it will be possible to make patient-related or hospital-related decisions, such as, but not limited to, ending hospitalization or treatment, changes in the treatment regimen, assigning a certain disability level to the patient, changing the function of the orthotic system from a rehabilitative device to an assistive device.

Control method of multi-jointed orthosis with more that 2 joints and 3 actuators. Start of all computing and/or program control activity begins with calibration that is taken action soon after the orthotic device and/or at list one of it subsystems strapped on the user's body and secured. As soon as the user presses on the activating button the subcomponents are commanded to be arranged in their default calibrating positions starting from the elbow subsystem and on.

Figure 9:
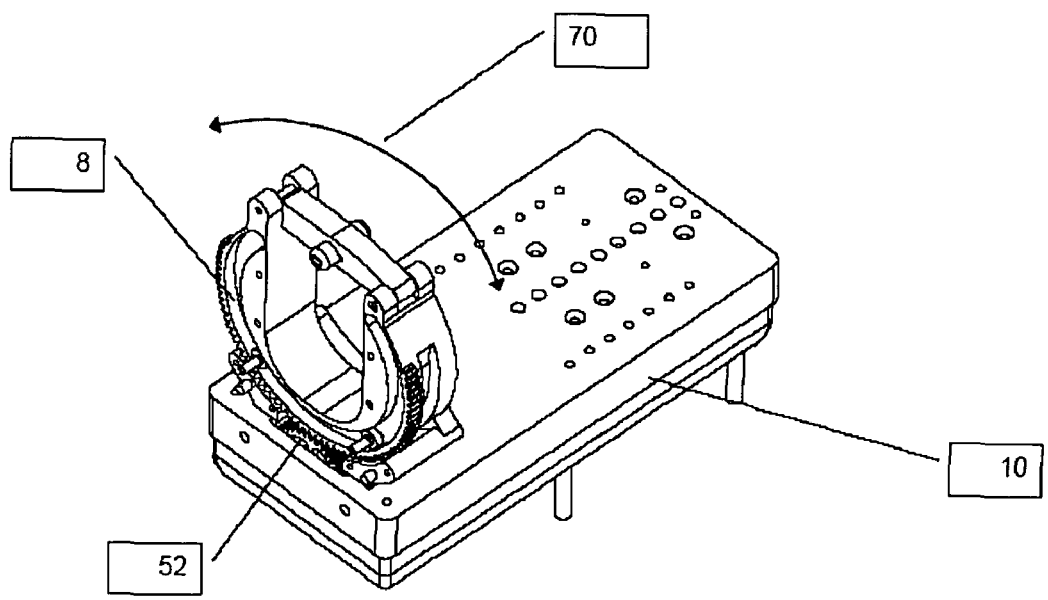
FIG. 9 is a perspective view of a forearm section of the elbow sub system shows on section 9a the composing of the wrist holding ring and on section 9a reveals the position of the wrist holder gear.
Figure 10:
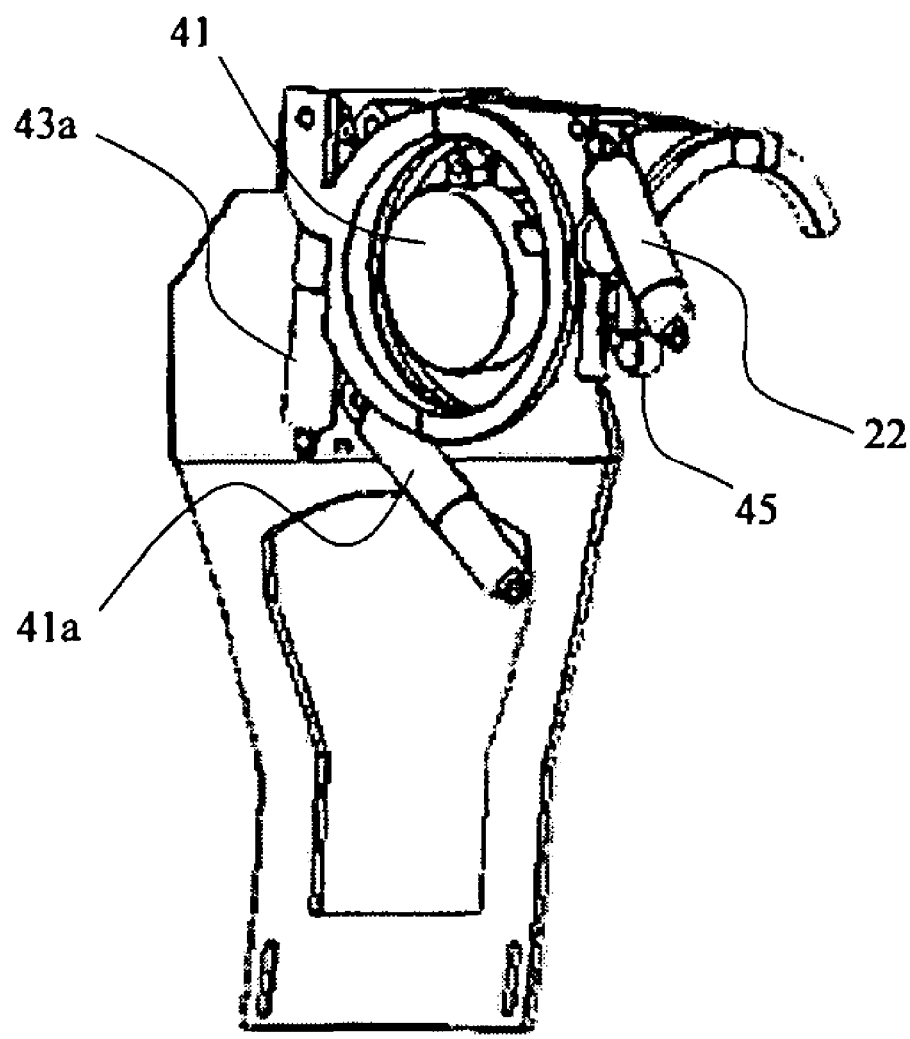
FIG. 10 is a detailed drawing showing the shoulder mechanism of the shoulder subsystem with emphasis on its actuation mechanism physical location and operational association of operational elements of the said subsystem system as shown assembled on the invented device on FIG. 2 and FIG. 3.
Figure 11:
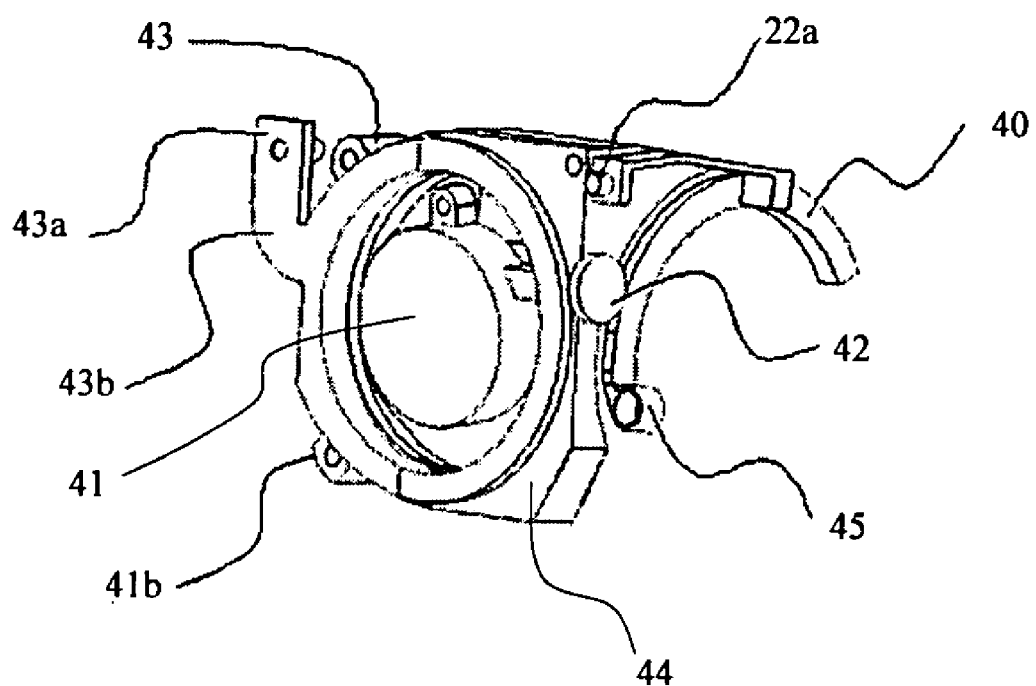
FIG. 11 shows a separated view of the shoulder subsystem mechanism with emphasis on its axels gears and operational parts.

The elbow subsystem is positioned automatically by memory in a way that the forearm chassis 10 is positioned in 90 degrees to the arm chassis 4, while the wrist holder ring 8 is placed perpendicularly to the forearm chassis as illustrated on FIG. 9 so that it could be turned from 0 degrees to +90 degrees to the right or −90 degrees to the left to enable performance of pronation and/or supination. The entire said subsystem is arranged automatically by memory order to be hung vertically by the arm shoulder axel 21 from the hinge 45 in a plain parallel to the body as the forearm protrudes forward in front of the body. Only than; first calibrations automatic actions starts by scaling the human forearm, using the forearm chassis as a scale plate and the arm load cell sensor for actual weight scaling and the scaling data are fed to the memory. Yet another scaling is done consequentially of the entire Elbow sub system from fingers to the arm at the said given angles and plains and the scaling data is also fed to the memory.

The invented orthodynamic program uses the data of the said calibration to regulate the level of power needed for actuating the rotation of each part around its specific axel, and/or at list two subsystems that are connected with an axel around their designed work plain. The regulation of motion and the power needed to exert the motion by adding or subtracting power to the actuators, thus, controlling and regulating the duration of rotation of the subsystem components in regard to each other and in regard to the subordinate and or upper subsystem axel.

Figure 32A:
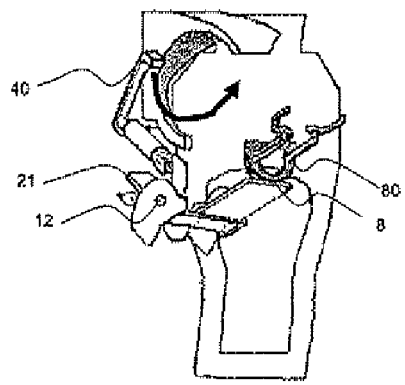
Figure 32B:
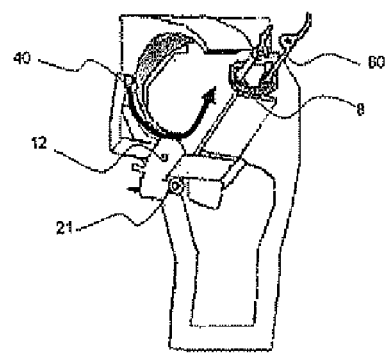
Figure 32C:
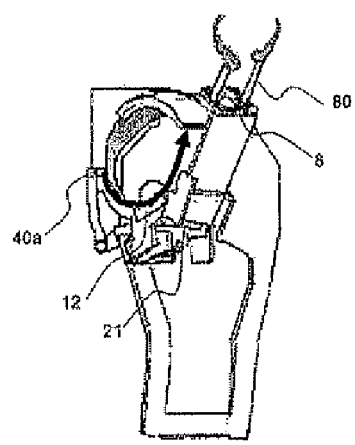

Yet more data is assessed at the said calibration mode: Passive range of motion active range of motion allowed ROM is operated. The operational data changes constantly at motion thus the following parameters are taken and processed: The actual weight of the living part of a limb does not change but the power required actuating and/or rotating that part in the range between its pre measured actual active range of motion and passive range of motion does change according to its angle in respect to gravitation. The said phenomenon illustrated well on FIG. 8 That illustrates the motion of the forearm 10 regarding the elbow axel 12 as the arm (Elbow subsystem) placed vertically to earth plain, the force needs to lift a limb tied to it from 90 degrees (Flexion) To 135 degrees is a function of the known forearm weight and additional force as required to rotate it in a lifting manner against gravitation. As the program allows the dropping of the forearm from 90 degrees to 0 it needs to subtract the forearm weight factor according to the degree of its extension aided by gravity. But the said explanation is not enough since each subsystem is capable of changing its position in respect to gravitational forces, i.e. when the entire arm subsystems are rotated around the main shoulder axel 40 as illustrated in FIG. 32 a, b, c the program sorts out and calculates the power needed to rotate the entire said assembly on its vertical plain by adding and subtracting the pre calibrated weight and gives necessary orders to the relevant shoulder actuator.

Figure 33A:
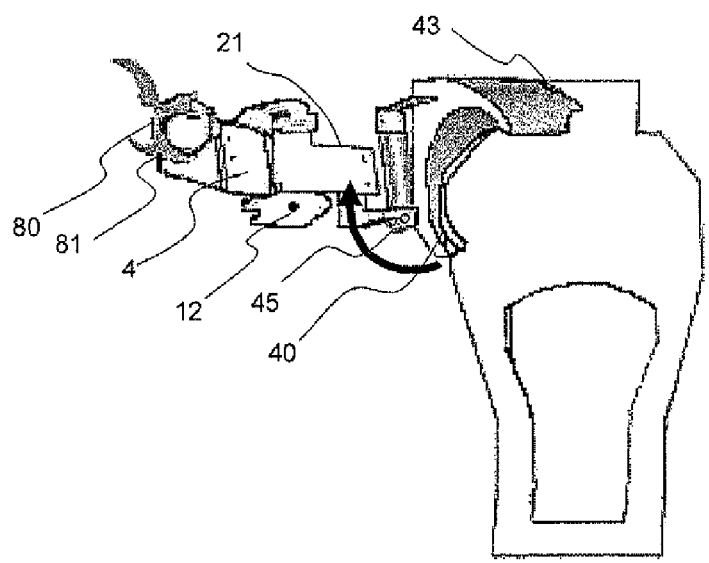
Figure 33B:
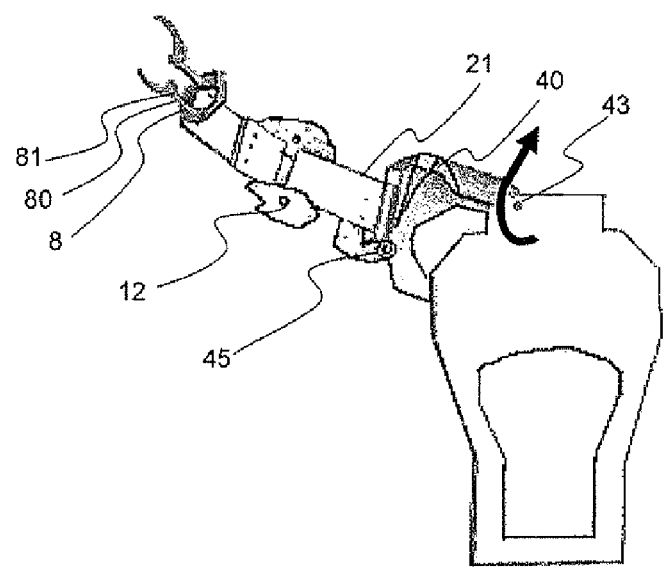

The same calibration and control method is applied for parts or subsystems rotated perpendicularly to the body as illustrated on FIG. 33. The said sensors measure the said changes in vertical forces (load) or radial forces (torque) and encoders sense the angle, their electronic signals are transferred to the main electronic board 100 that transmits them to the processor 101 which translates the said electronic signals to digital signals that are sent via the M board 102 to the memory control unit in the processor or the computer to be processed by the orthodynamic program to digital orders that are transmitted to the said processor that translated them to electronic signals that are transmitted via the said electronic board to the selector 3a that distribute hydraulic pressure to the relevant actuators that perform the said orders each in its own specific work plain.

The program does not allow under any events a rotation of a part or a subsystem or an entire assembly to be actuated beyond the pre calibrated distance between the active range of motion and the passive range of motion allowance. The program has also overriding safety features such as emergency stop button, and power limitation boundaries.

The present invention is a multi-joint portable orthosis system that performs pre-defined or user-controlled limb movements, collects data regarding limb movement, performs data analysis and displays representations of the data and data analysis results in real time, and modifies current operational parameters based upon such data so as to optimize the rehabilitative process performed by the system.

The following description will first discuss one subsystem of an orthotic system constructed and operative according to the principles of the present invention configured for rotation of the elbow and forearm (FIGS. 4-9), and then discuss the operation of the device in two different modes of operation, rehabilitative mode (FIGS. 15-27) and assistive mode.

Figure 4:
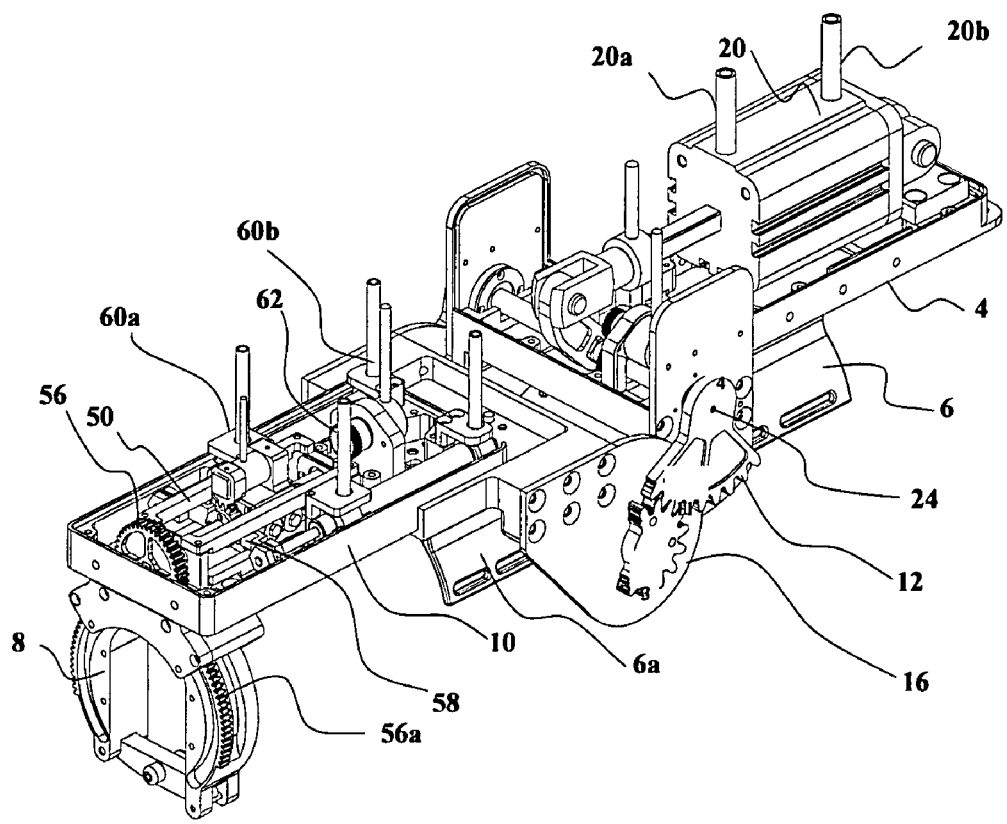
FIG. 4 shows the elbow subsystem with out covers—bottom view.
Figure 5:
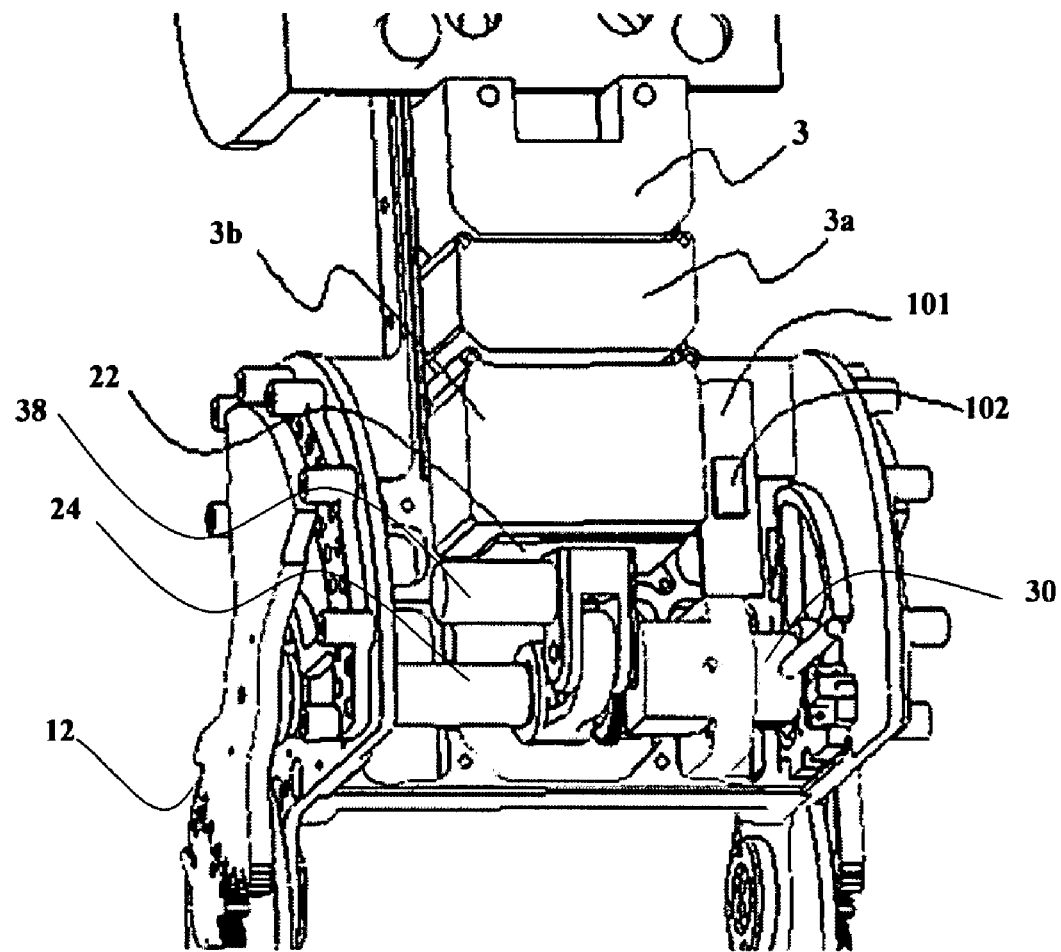
FIG. 5 shows the drive and control components: such as hydraulic selector, hydraulic pump, said component's actuating electric motor, electronic board, mother board and processor assembled on the arm chassis of the elbow subsystem.
Figure 6:
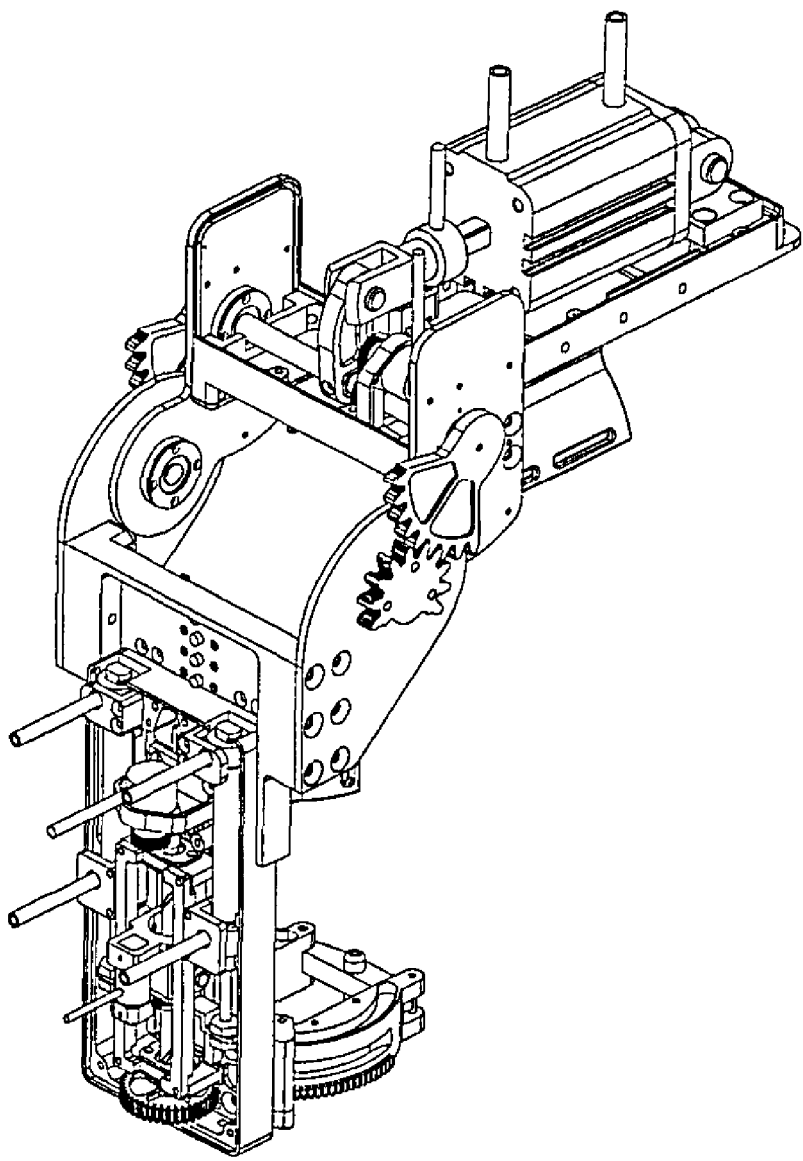
FIG. 6 is a perspective view of operational hydraulic actuator and elbow rotating gear elements at 90 degrees position deployed in the upper arm section of the Elbow sub system.

The said subsystem called Elbow subsystem of an orthotic system according to the teachings of the present invention illustrated in FIG. 4 includes an external actuating device 20, and control units controlled by an external computer and/or a memory controlled processor.

FIG. 4 illustrates the elbow subsystem actuated by external actuating device 20 constructed and operative according to the principles of the present invention. The upper arm section 4 of the Elbow subsystem is held on the upper arm of the patient by use of, preferably Velcro®, straps (not shown) used in association with the upper arm attachment element 6. The forearm, near the wrist, of the patient is placed into the forearm rotator called wrist holder 8, and the forearm section 10 of the external Elbow subsystem is held in place by use of, preferably Velcro®, straps (not shown) associated with the forearm attachment element 6a. The place of the external Elbow subsystem of the arm of the patient is such that a first axis of rotation 12 of the rotatable interconnecting hinge 16, connecting the upper arm section 4 to the forearm section 10, lies substantially on the axis of rotation of the patient's elbow joint. The first axis of rotation will be referred to here in the description as the "elbow axis of rotation." 24 In such a deployment, activating rotation of the external actuating device about the elbow axis of rotation rotates the patients elbow joint.

Figure 3:
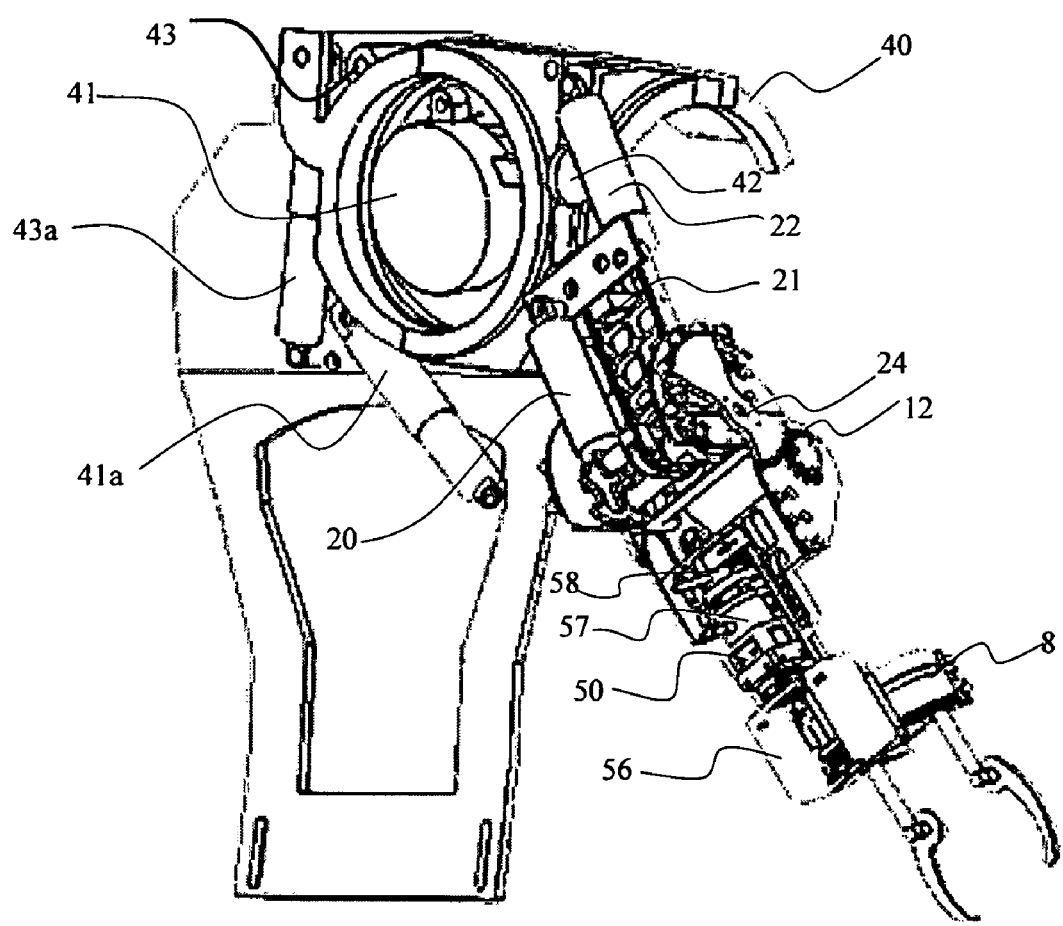
FIG. 3 shows a full blown drawing of the back side view of the disclosed invention operative according to the principles described in the following chapters in farther details.

FIG. 8 from 3a to 3d illustrate rotation of the external actuating device about the elbow axis of rotation. FIG. 3a illustrates 0° of rotation; FIG. 3b illustrates 20° of rotation 120; FIG. 3c illustrates 90° of rotation 122; and FIG. 3d illustrates 135° of rotation 124.

Axial rotation of the patient's forearm is accomplished by rotation of the forearm rotator 8, which is configured so as to rotate 180° about a second axis of rotation that runs substantially longitudinally through the center of the forearm and substantially perpendicular to the elbow axis of rotation. The second axis of rotation will be referred to here in the description as the "forearm axis of rotation."

Figure 7:
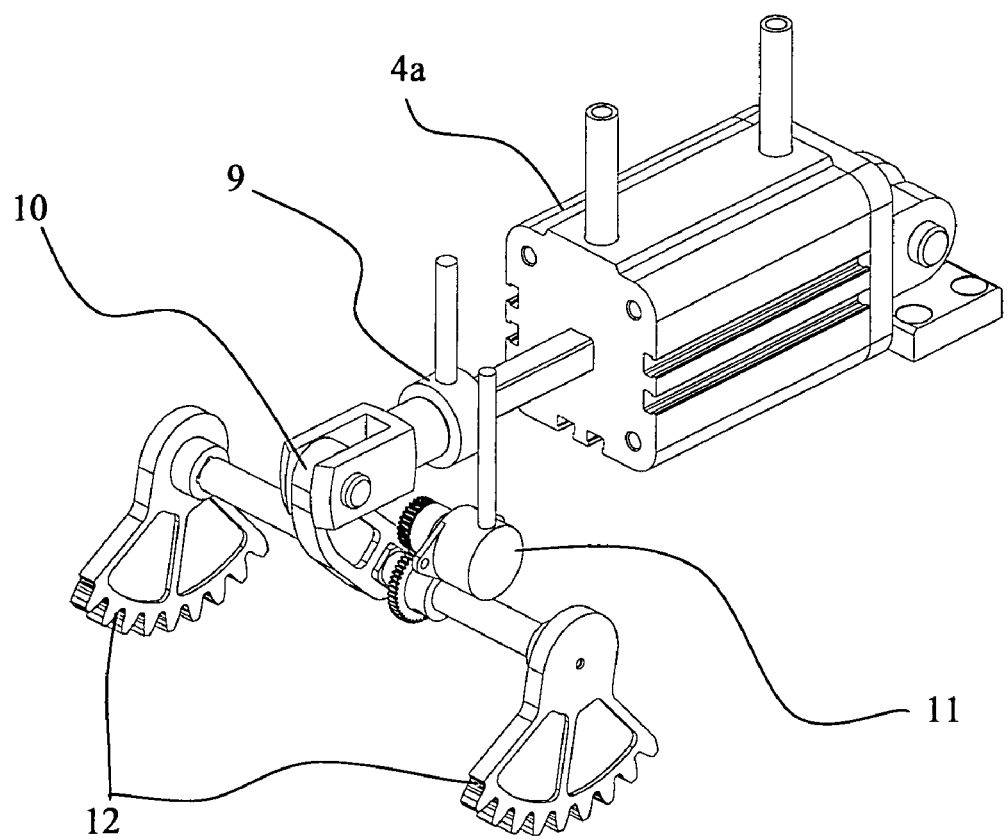
FIG. 7 is a perspective view of operational actuating and driving gear mechanism of the forearm deployed on the arm chassis section of the elbow sub system.
Figure 8A:
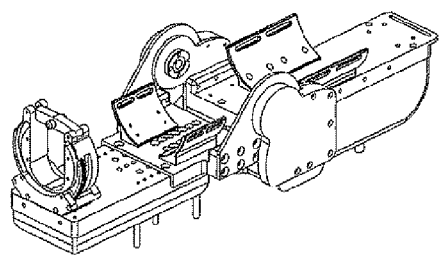
FIG. 8 shows trough drawing 8a to 8d are a series of perspective views of the elbow sub system and components showing rotation of an external actuating device though a range of rotation from 0° to 135°.
Figure 8B:
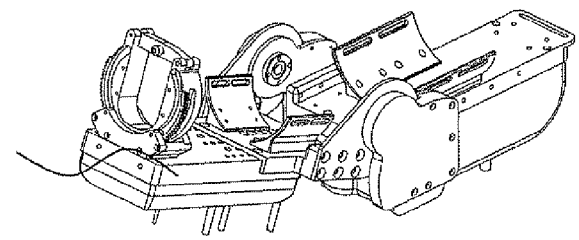
Figure 8C:
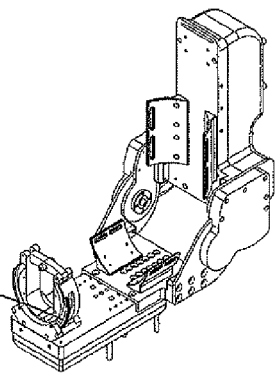
Figure 8D:
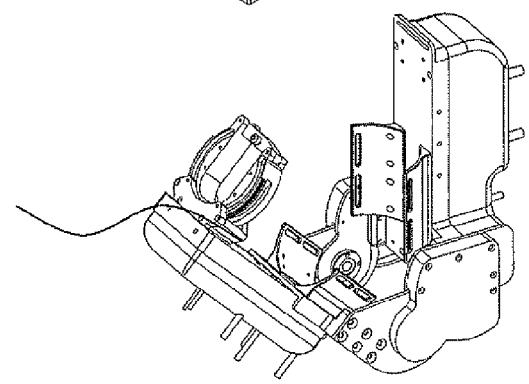

FIGS. 7 (perspective) and 5 (top elevation) provide similar views of mechanical elements of the external actuating device with out housing covers, and are therefore similarly numbered. The elbow rotation mechanism, located in the upper arm section 4, provides rotation about the elbow axis of rotation whereby linear movement of piston 20 in association with lever 22 causes the rotation of axle 24 and thereby rotation of gears 12 (see also detail FIG. 6). Piston 20 is preferably a bi-directional hydraulic piston in fluid communication with a computer controlled selector directing pressurized hydraulic fluid though hydraulic lines 20a and 20b. Data collection elements such as but not limited to, a tension/compression load cell 28 and encoder 30 may also be associated with the elbow rotation mechanism, and be in data communication with the data processor in the control unit or with the external computer, to provide real time data for, by non-limiting example, real time device operational modifications, and treatment evaluation and assessment.

Figure 28A:
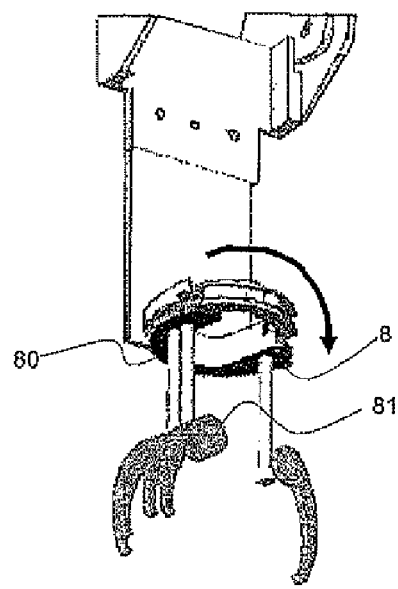
Figure 28B:
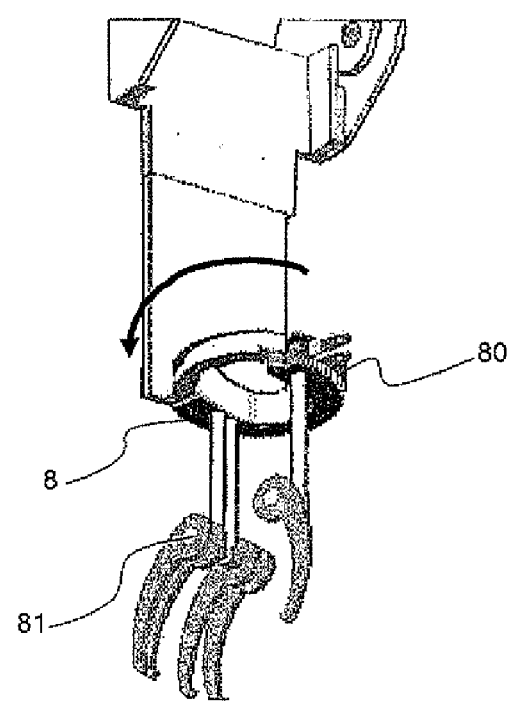
Figure 29A:
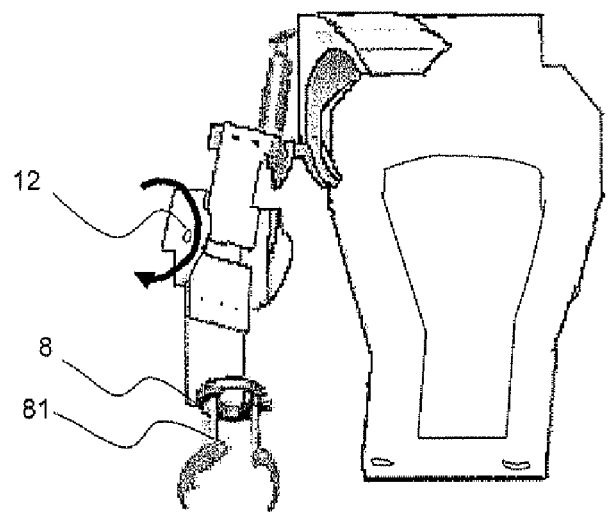
Figure 29B:
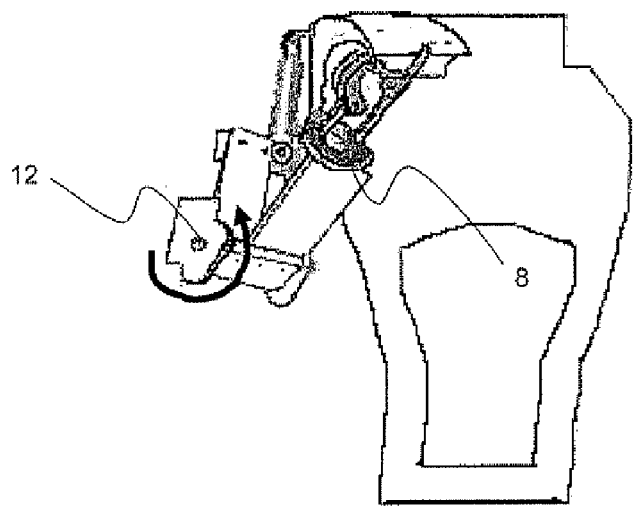

The forearm rotation mechanism, located in the forearm section 10, provides rotation about the forearm axis of rotation whereby linear movement of rotational electric hydraulic and/or electric actuator 50 causes the rotation of gear 56, which in turn rotates the forearm 8 rotator gear 56a (see also detail FIG. 9) throughout a range of substantially 180°, as indicated by arrows in FIG. 28. Pistons 50 is preferably bi-directional hydraulic piston in fluid communication with a computer controlled selector 3b illustrated on FIG. 5. Data collection elements such as but not limited to, a load cell 58 and encoder 62 may also be associated with the elbow rotation mechanism, and be in data communication with the microprocessor, to provide real time data for, by non-limiting example, real time device operational modifications, and treatment evaluation and assessment.

Figure 13:
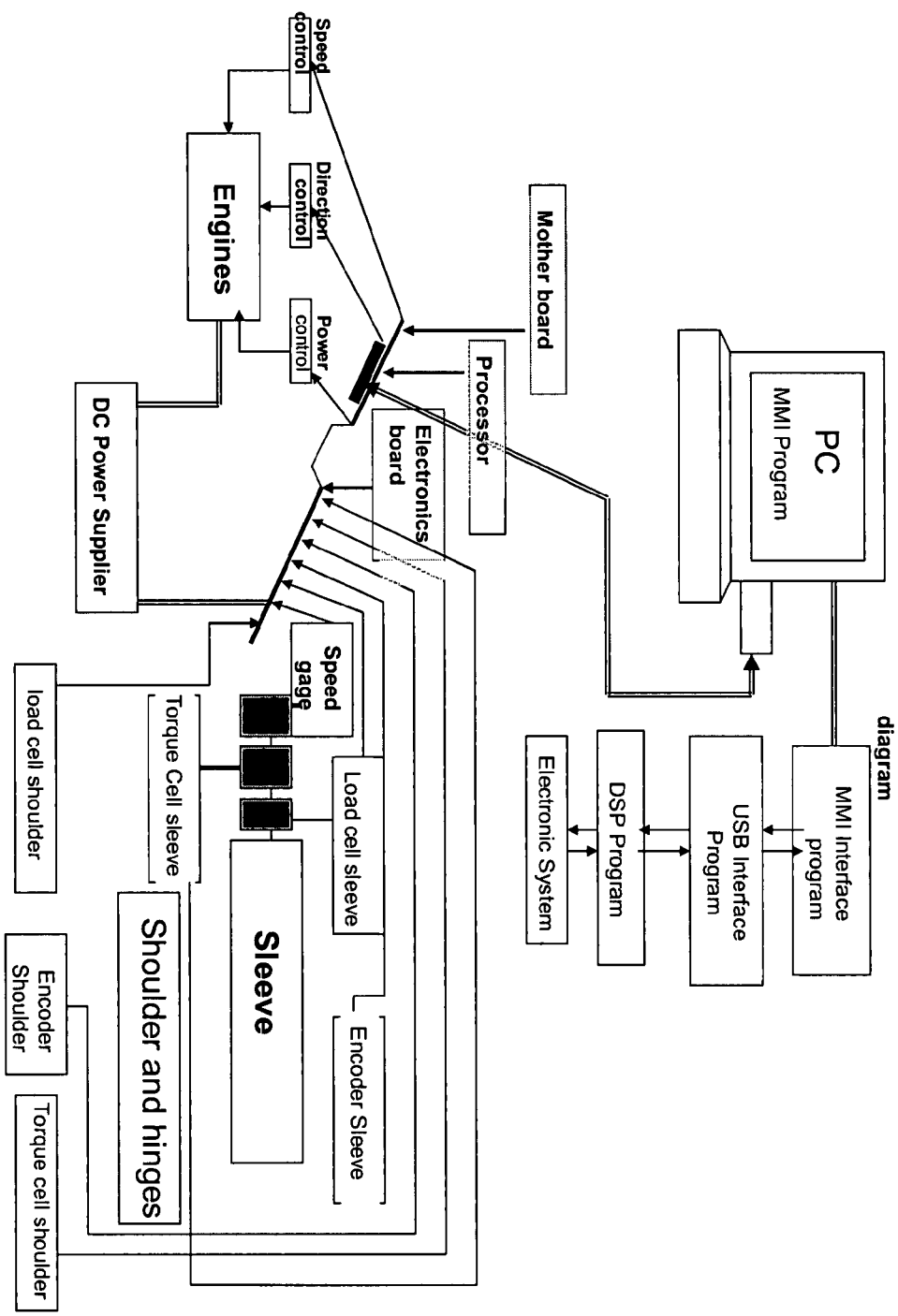
FIG. 13 shows a flow chart assistive upper limb—software command and control block diagram
Figure 14:
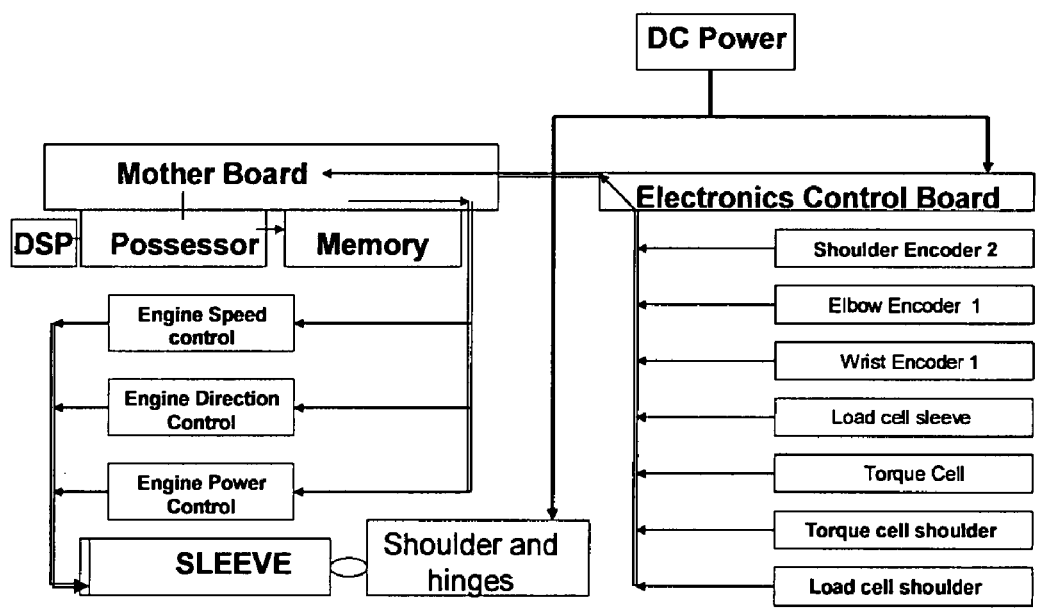
FIG. 14 shows a block diagram orthodynamic assistive assemblies at work—Block Diagram.
Figure 15:
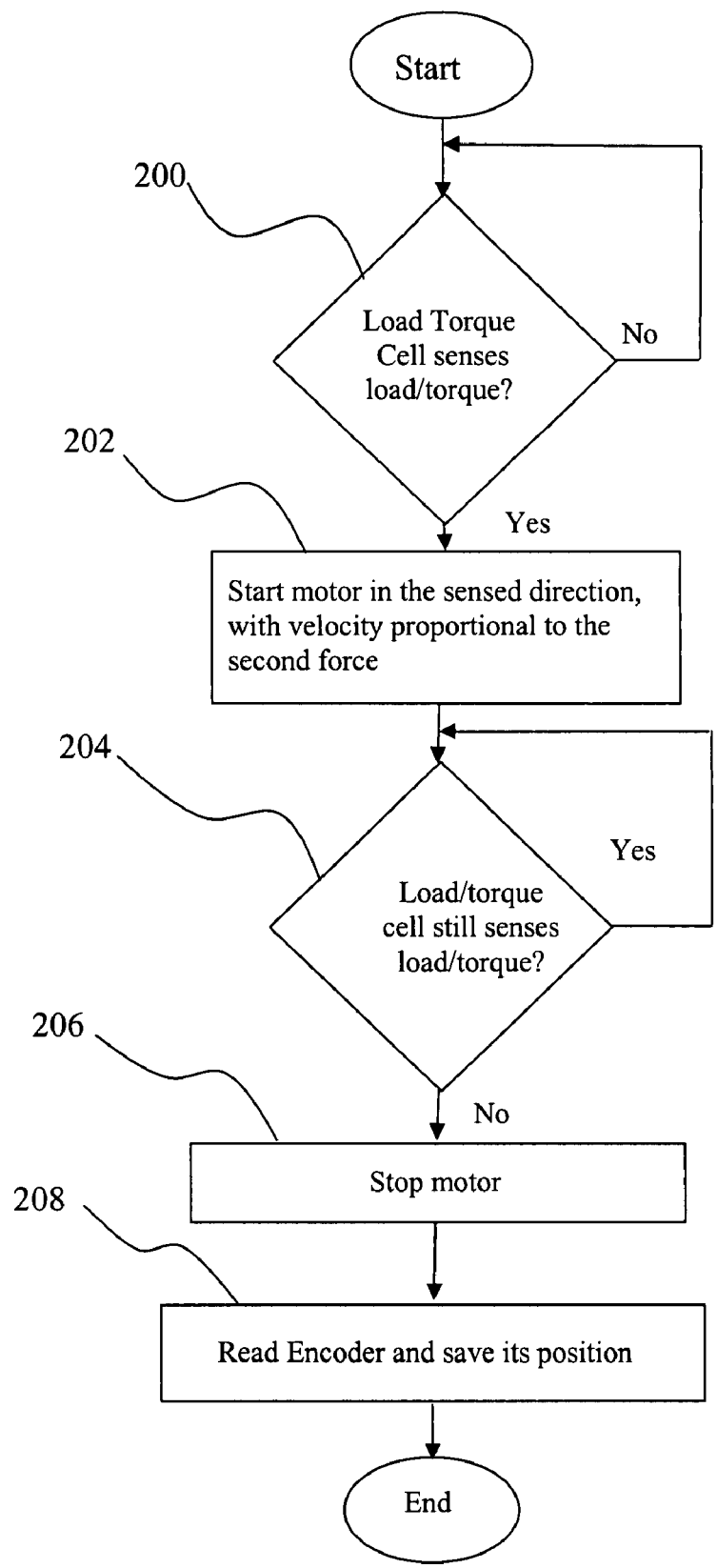
FIG. 15 shows a flow chart of an assessment of active range of motion according to the teachings of the present invention.

The block diagram of FIG. 14 illustrates the association of main operational elements of the present invention subsystem parts and their physical location within this embodiment of the said present invention. Therefore, associated with the upper arm section 4 is a controller, a torque limiter, a rotary to linear converter, an injector piston, a piston, an elbow rotation mechanism, a pressure sensor, an encoder to measure angle of deployment, and a load cell. The controller, torque limiter, rotary to linear converter, and injector piston are physically located in the remote control unit 500. Likewise, the piston 20, elbow rotation mechanism (including lever 22, axle 24 and gears 26), pressure sensor, encoder 30, and load cell 28 are physically located in the upper arm section 4 of the external actuating device 2. Similarly, associated with the forearm section 10 is a controller, a torque limiter, a rotary to linear converter, an injector piston, a pistons, a forearm rotation mechanism, a pressure sensor, an encoder, and a load cell. The pistons 50 and 50', forearm rotation mechanism (linear slide bolt 52, helical rod 54, gear 56, and forearm rotator 8), pressure sensor, encoder 62, and load cell 58 are physically located in the forearm section 10 of the external actuating device 20. Also illustrated on FIG. 13 how data from the individual data collection elements is sent to the microprocessor in real time such that the current and/or on going functions of the external actuating device may be modified, responsive to the data, by modifying at least one operational parameter of a set of operational parameters during an uninterrupted treatment session.

It should be noted that while the preferred elbow sub system herein and other subsystems incorporated in the disclosed invention described relates to hydraulic actuators, however, the use of any suitable actuators known in the art is within the scope of the present invention.

Turning now to the use of an orthotic system of the present example of the elbow subsystem invention employed in a rehabilitative mode, the present invention provides for range of motion assessment, classical muscle testing and a treatment regimen. Here, for the ease of discussion, the description will relate, by non-limiting example, to the elbow and forearm of a patient.

To assess a patient's active range of motion, the patient is asked to move his arm so as to rotate his elbow joint. Sensors deployed on the external actuating device detect the amount and direction of the force. The data is analyzed and the external actuating device is advanced correspondingly as long as force is detected. This procedure, as illustrated in the non-limiting flowchart example of FIG. 15 for the patient's elbow joint movement, is repeated also for assessing the patient's forearm axial range of motion. As shown, when force is sensed by any one individual or combination of, load/torque cells 200 the external actuating device is advanced in the corresponding direction with proportional velocity 202. That is, the velocity may be slightly less than would have been normally achieved by the amount of force sensed so that force against the sensor will still be detected. Advancement of the external actuating device continues as long as force is sensed 204. As seen here, the force data is analyzed in real time and the corresponding operational function of the external actuating device are modified in real time so as to meet the predefined therapeutic parameter of advancing the external actuating device at a rate that will continue to detect any force exerted by the patient. That is to say, the velocity of the external actuating device is varied based on the data received from the load/torque cells. When force is no longer detected by the load/torque cells, advancement of the external actuating device is stopped 206 and the relative position of the sections in recorded 208 and the data is stored 209 and added to the patient's database.

Figure 16:
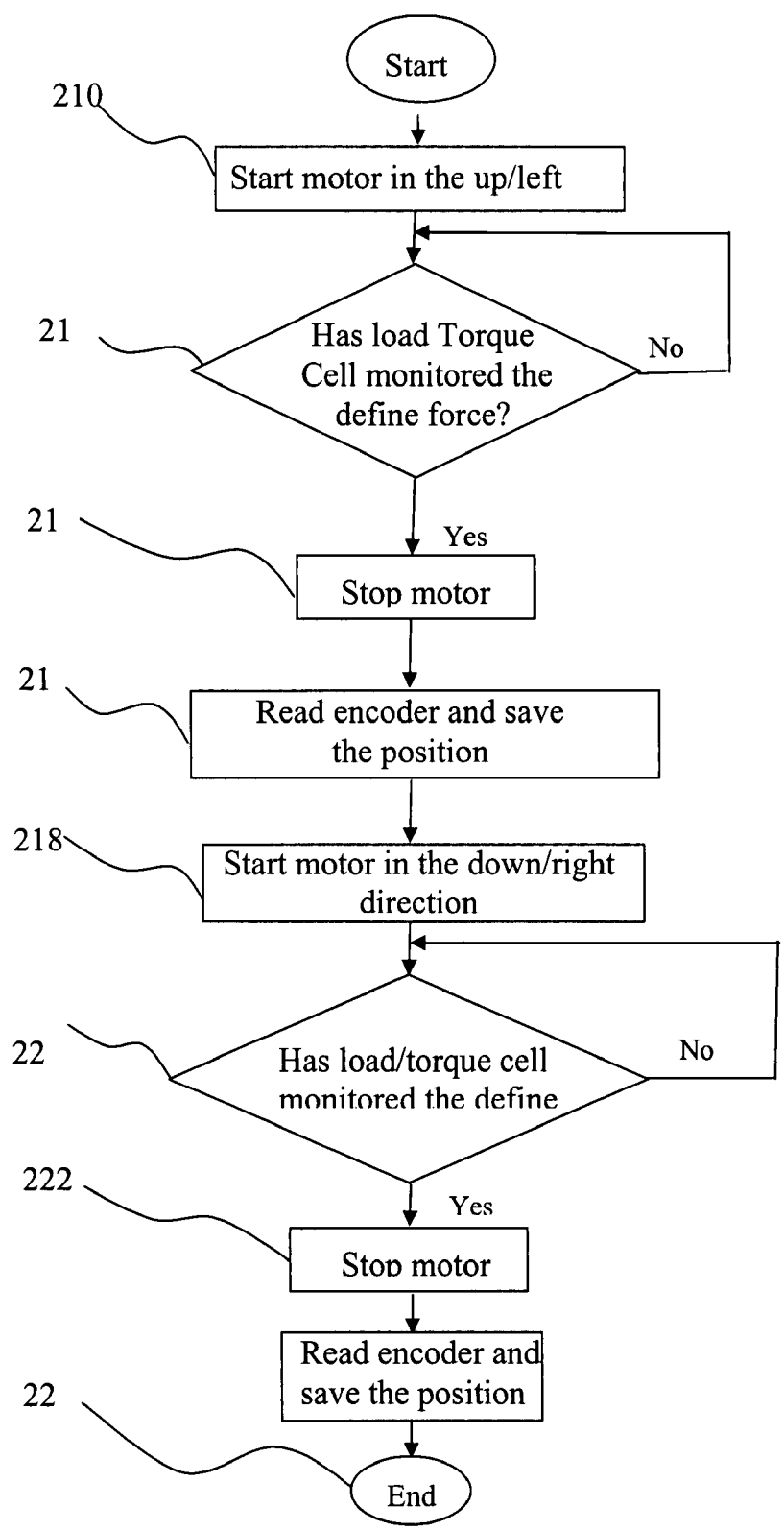
FIG. 16 shows a flow chart of an assessment of passive range of motion according to the teachings of the present invention.

Assessment of passive range of motion, as illustrated in the non-limiting flowchart example of FIG. 16, entails the steps of deploying the external actuating device on the patient in a benign angular deployment, advancing the external actuating device in one direction 210, such as up or left for example, until a predefined level of resistance force is detected 212, stopping advancement 214, the relative position of the sections is recorded as a boundary of the passive range of motion 216. The process for determining the corresponding boundary entails the steps of reversing direction of the external actuating device 218, passing through the beginning angle and advancing until a predefined level of resistance force is detected 220, stopping advancement 222, the relative position of the sections is recorded as a boundary of the passive range of motion 224. All of the data from the session is saved 225, and may be added to the patient's treatment/assessment database.

Figure 12:
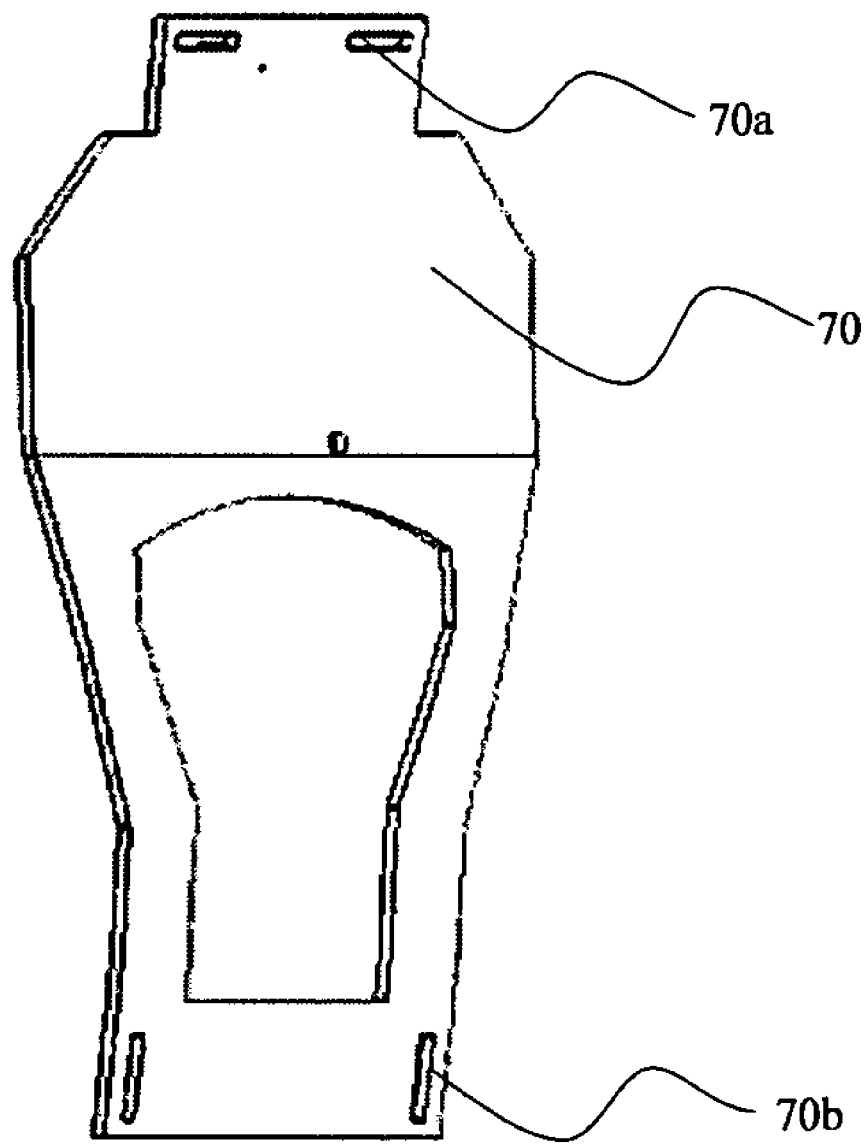
FIG. 12 shows that harness chassis designed like a backpack enabled to be strapped and adjusted to a human body capable of carrying and harnessing two of the disclosed upper limb devices (right and left)
Figure 17:
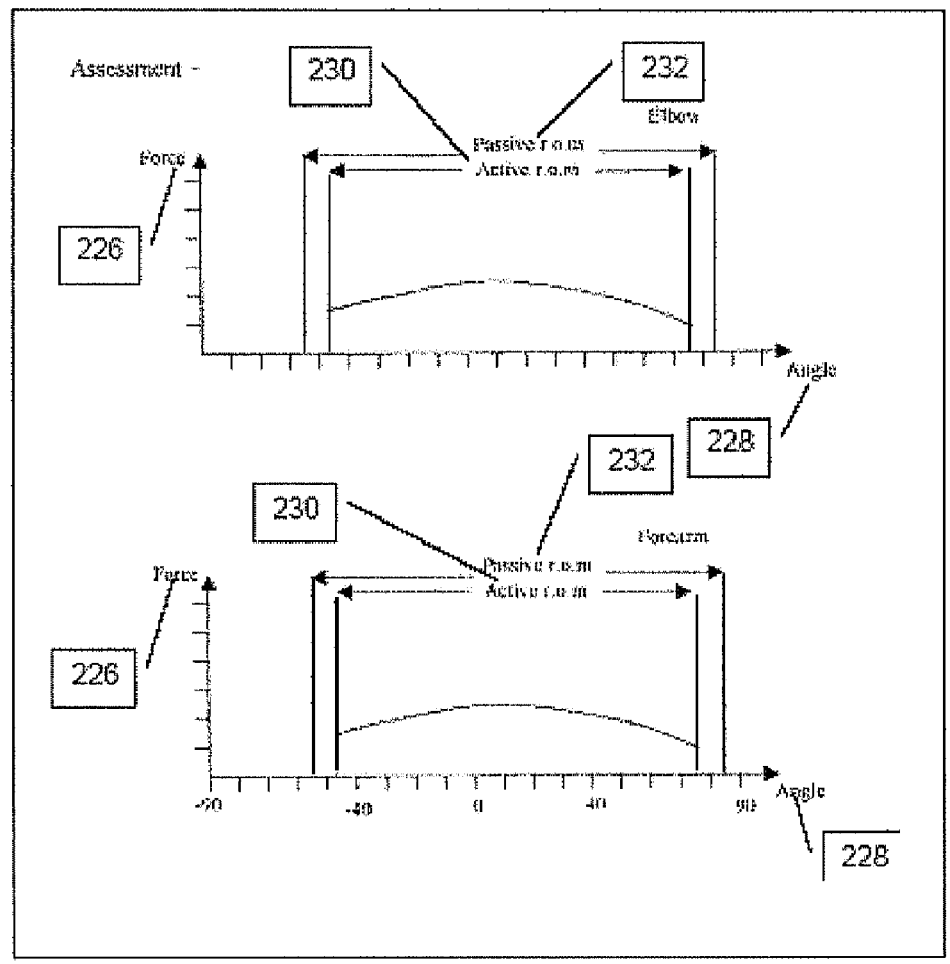
FIG. 17 shows a graphic representation of data collected during an assessment of active range of motion and/or passive range of motion according to the teachings of the present invention.

Data collected regarding the patient's ranges of motion may be displayed as a graph such as the non-limiting examples of FIG. 17, where force 226 is plotted as a function of the angle 228. It should be noted that the full ranges of both the passive 230 and active 232 ranges of motion are shown in the graphs of FIG. 12, however, according to the present invention each of the parameters may be displayed individually. Further, the data may be displayed in real time during the testing session. That is to say, it is possible to watch the graph being constructed substantially as the data is supplied to the microprocessor, as the assessment procedure is in progress. Substantially any data that may be represented in graph form may be displayed in real time.

Figure 18:
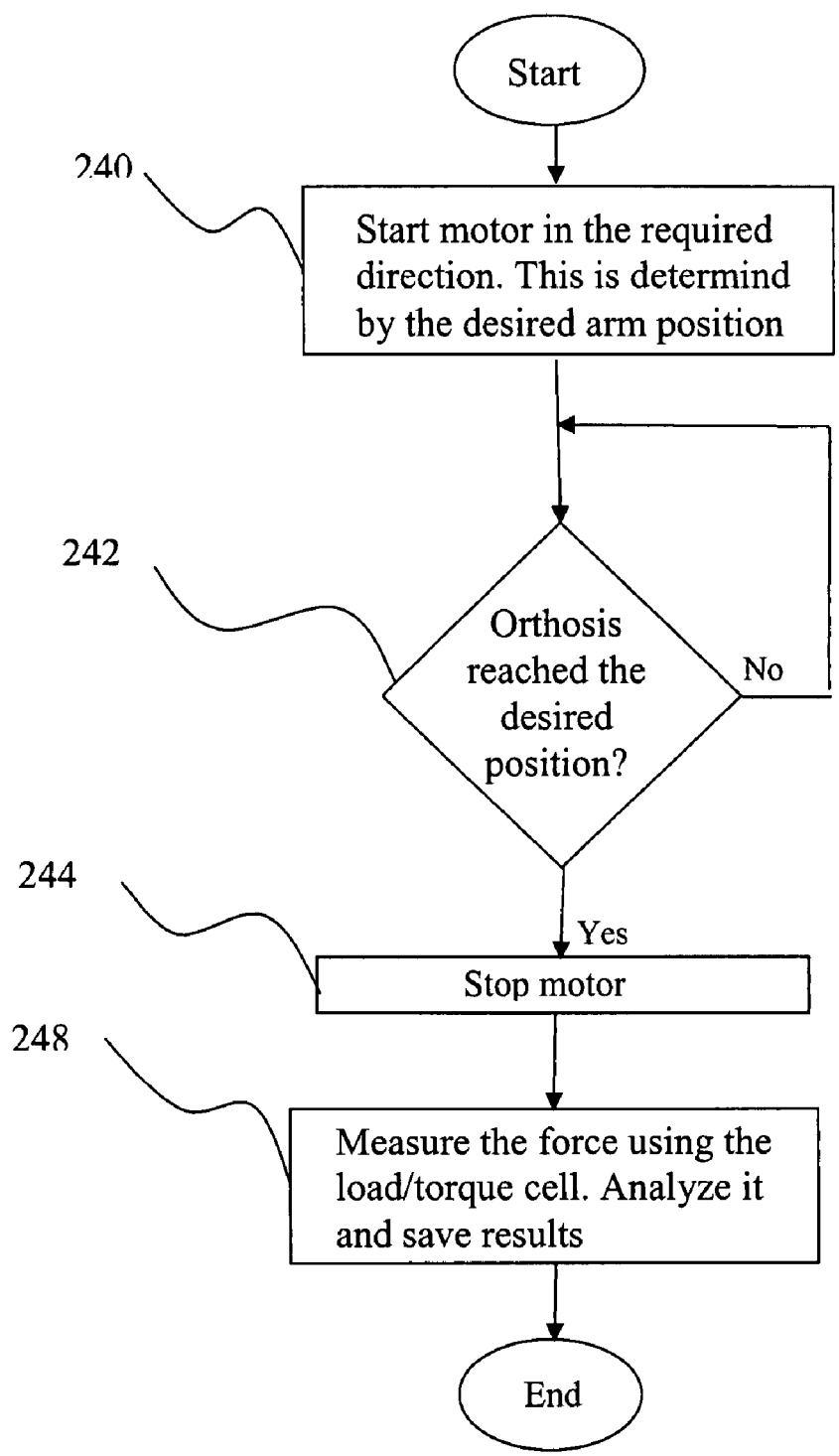
FIG. 18 v a flow chart of classical muscle testing according to the teachings of the present invention.

Classic muscle testing, as illustrated in the non-limiting flowchart example of FIG. 18, entails bringing the external actuating device to a series of predefined angular deployments (steps 240, 242 and 244) and measuring the force the patient is able to apply to the device 248. Data collected during classical muscle testing may be displayed in chart form, such as the non-limiting example illustrated in FIG. 14, which provides testing in three different positions 250 each for both the elbow 252 and the forearm 254, and records the actual force applied 256 and the force rating on a force scale of 0-5 258. All of the data from the session is saved 249, and may be added to the patient's treatment/assessment database.

A treatment regimen, as determined by a doctor or therapist, may include any one of or a combination of strain/counter strain, isometric concentric, isotonic concentric, hold and relax, and PNF (Proprioceptive Neuromuscular Facilitation) exercises.

Figure 20:
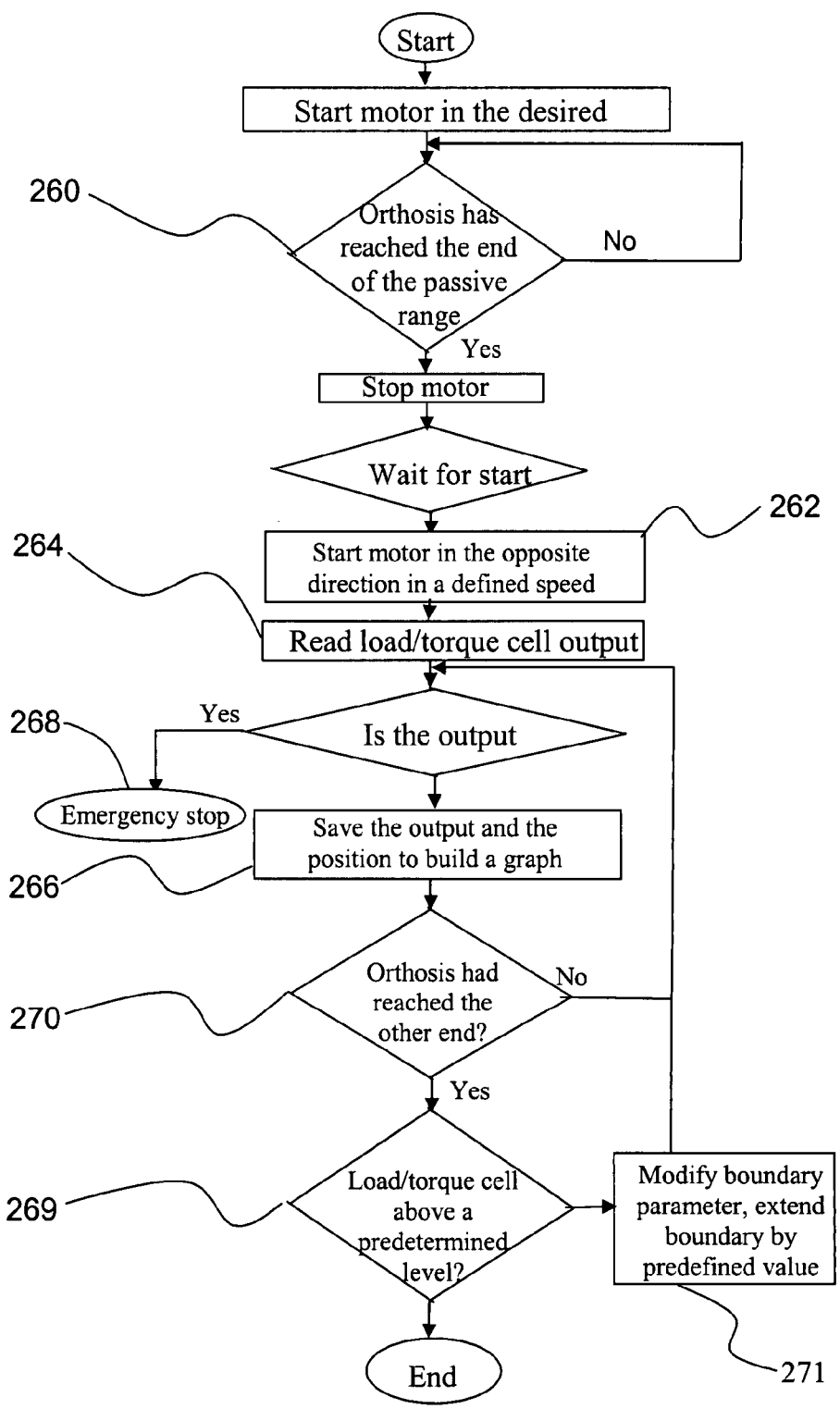
FIG. 20 shows a flow chart of a strain/counter-strain treatment regimen according to the teachings of the present invention.

As the non-limiting flowchart example of FIG. 20 illustrates, operation of the orthotic system in a strain/counter-strain exercise mode according to the teachings of the present invention. The external actuating device is brought to one boundary of the patient's passive range of motion 260, and then moved in one direction through the full passive range of motion 262-270. In this manner, four different muscle groups, forearm flexors, extensors, supinators and pronators, may be isolated during treatment and worked separately, either during different treatment sessions or at different times during a single session. Data from the load and/or torque cells is monitored at a substantially constant rate 264 and the data is analyzed for display in a graphic representation 266. If a predefined emergency level of resistance in encountered, advancement of the external actuating device is stopped 268. As part of the full exercise, or as an optional subroutine, when the opposite boundary is reached, if the patient's resistance to movement is below a predefined level 269, the boundary parameter is modified 271. Modification may be, by non-limiting example, extension of the boundary by a predefined increment or until a predefined level of resistance is met. If during the extension of the boundary, an emergency level of resistance is encountered, the new boundary may be sent at a point before the emergency level of resistance was encountered. All of the data from the session is saved 267, and may be added to the patient's treatment/assessment database.

Figure 21:
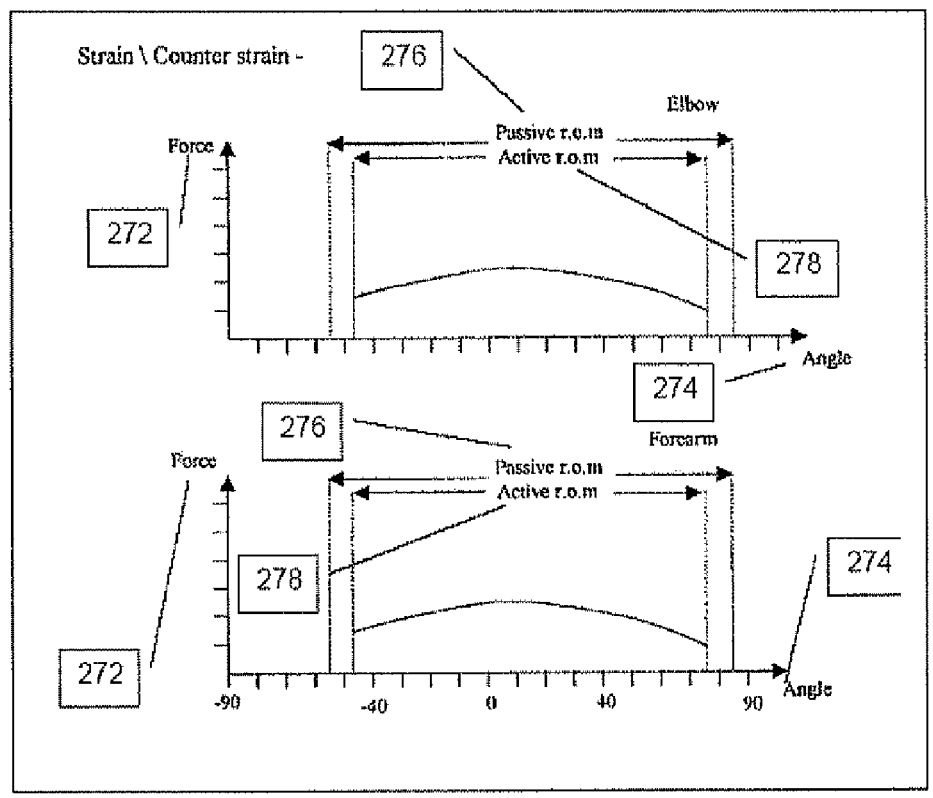
FIG. 21 shows a graphic representation of data collect during a strain/counter-strain treatment session according to the teachings of the present invention.

Non-limiting examples of graphs displaying data collected during strain/counter-strain exercises are shown in FIG. 21, where force 272 is shown as a function of angle 274. Graphs for movement through the passive 276 and active 278 ranges of motion may be displayed individually or concurrently. Alternatively, data from the current session may be display concurrently with data from previous treatment or assessment sessions, data in the patient's database or the system's expert knowledge database. It should be noted that the ability to concurrently display data from any single previous treatment or assessment session, any derivative of data in the patient's personal database, or the system's expert knowledge database, is true for all of the graphs, table and charts herein discussed and is considered a principle of the present invention.

Figure 22:
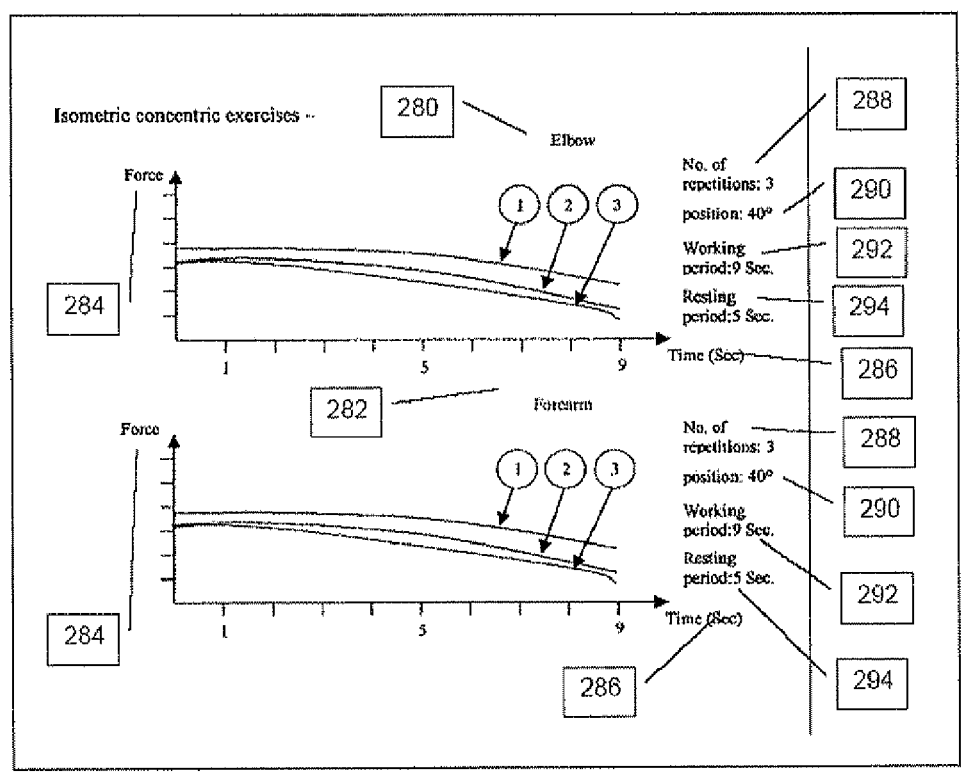
FIG. 22 shows a graphic representation of data collect during an isometric concentric exercise treatment session according to the teachings of the present invention.

The procedure described above in regard to FIG. 18 for classical muscle testing may be repeated in the treatment regimen as an isometric concentric exercise. When the procedure is used as a treatment, the data displayed, as illustrated in FIG. 22 may include information relating to the elbow 280 and the forearm 282 individually in the same display. Each graph shows force 284 as a function of time 286. Other information that may be displayed may include, by non-limiting example, the number of repetitions 288, the angle of deployment at which the exercise was done 290, the duration of the exercise 292 and the rest period between repetitions 294.

Figure 23:
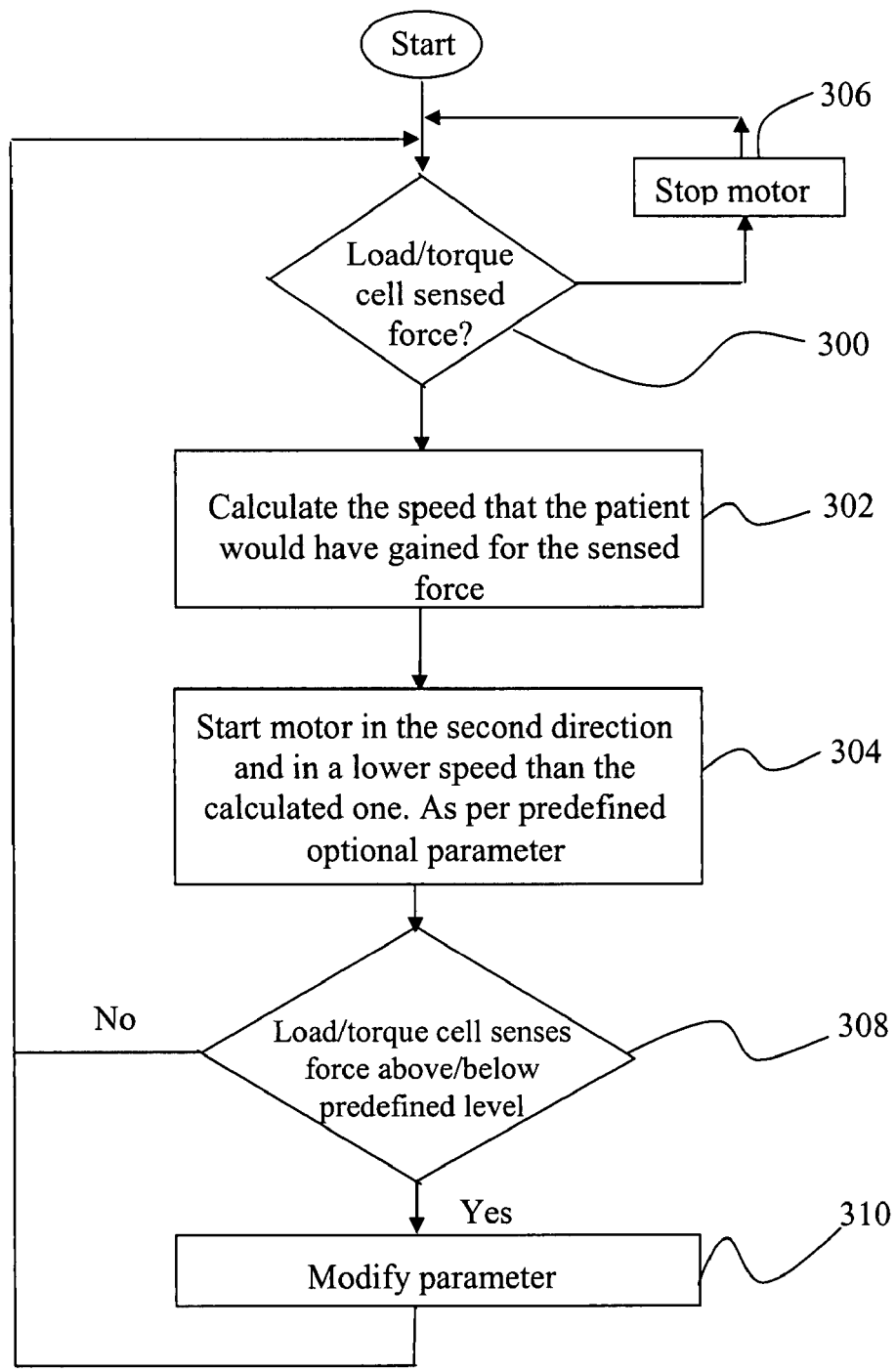
FIG. 23 shows a flowchart of an isotonic concentric exercise treatment session according to the teachings of the present invention.

The flowchart of FIG. 23 shows a non-limiting example of an Isotonic exercise according to the teachings of the present invention. The patient is told to move his arm so as to, by non-limiting example, rotate his elbow joint. The force of the patient is sensed by the load cell and/or torque cell 300. The velocity normally achieved by such force is calculated 302 and the external actuating device is advanced at a rate lower than that calculated 304, as per a predefined parameter so as to provide resistance to the patient. If the force sensed is above or below a predefined level 308, then the predefined parameter of step 304 is modified is step 310. The motions outlined in the above steps are followed until no force is detected, and then the advancement of the external actuating device is stopped 306. All of the data from the session is saved 311, and may be added to the patient's treatment/assessment database. It will be readily appreciated that the numerous operational parameters may be monitored and varied during an individual treatment session.

Figure 24:
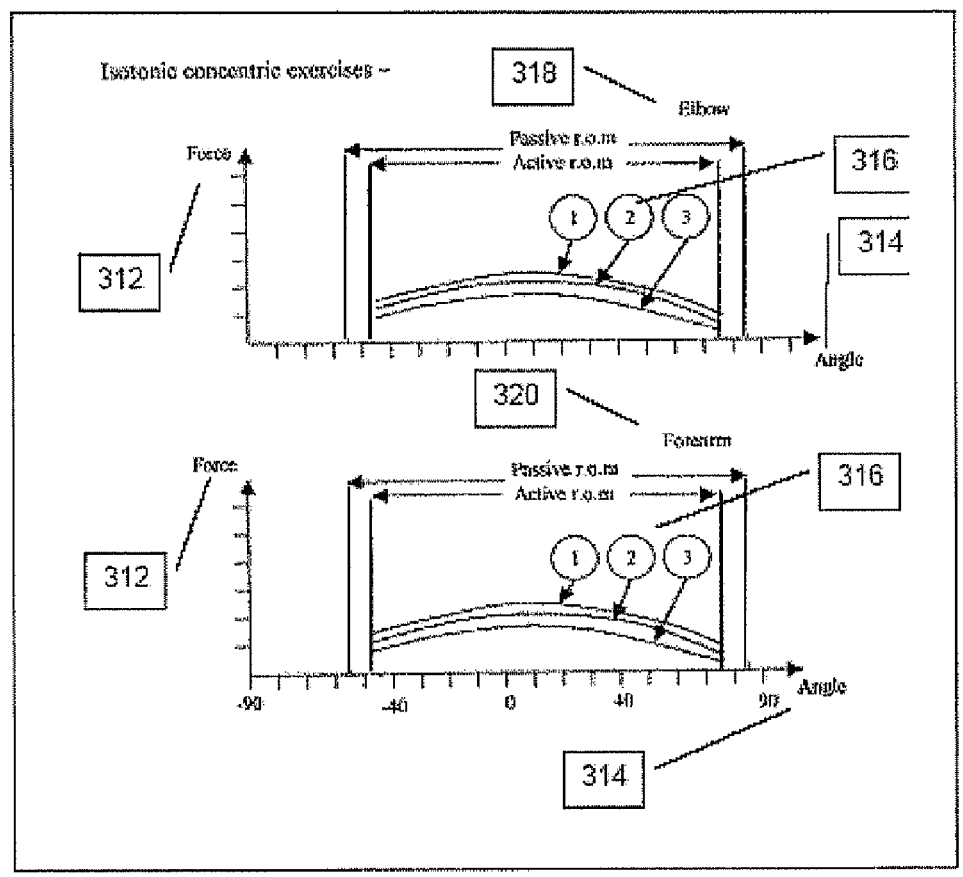
FIG. 24 shows a graphic representation of data collect during an isotonic concentric exercise treatment session according to the teachings of the present invention.

A non-limiting example of a treatment regimen may be maintaining the predefined constant proportional resistance. That is, predefining that the external actuating device maintains constant rate of resistance of, by non-limiting example, 80% of patient applied force. If, however, the force applied by the patient rises above or falls below a predefined optimal rehabilitative level the proportion of resistance is modified accordingly. That is to say, if the patient applied force falls below a predefined optimal rehabilitative level the rate of resistance is modified to, for example 75% of the patient applied force. Conversely, if the patient applied force rises above a predefined optimal rehabilitative level the rate of resistance is modified to, for example 90% of the patient applied force. Therefore, according to the teaching of the present invention, if during course of a treatment session the patient applied force rises above or falls below a predefined optimal rehabilitative level, the parameter of proportion of resistance is modified without interrupting the ongoing treatment session. As illustrated in FIG. 24, the data displayed for isotonic concentric exercises may be displayed as a graphic depiction of the force 312 exerted by the patient as a function of the angle 314, and the number of repetitions 316. Graphs for each repetition may be displayed concurrently, and separate graphs may be displayed for the elbow 318 and the forearm 320.

Figure 25:
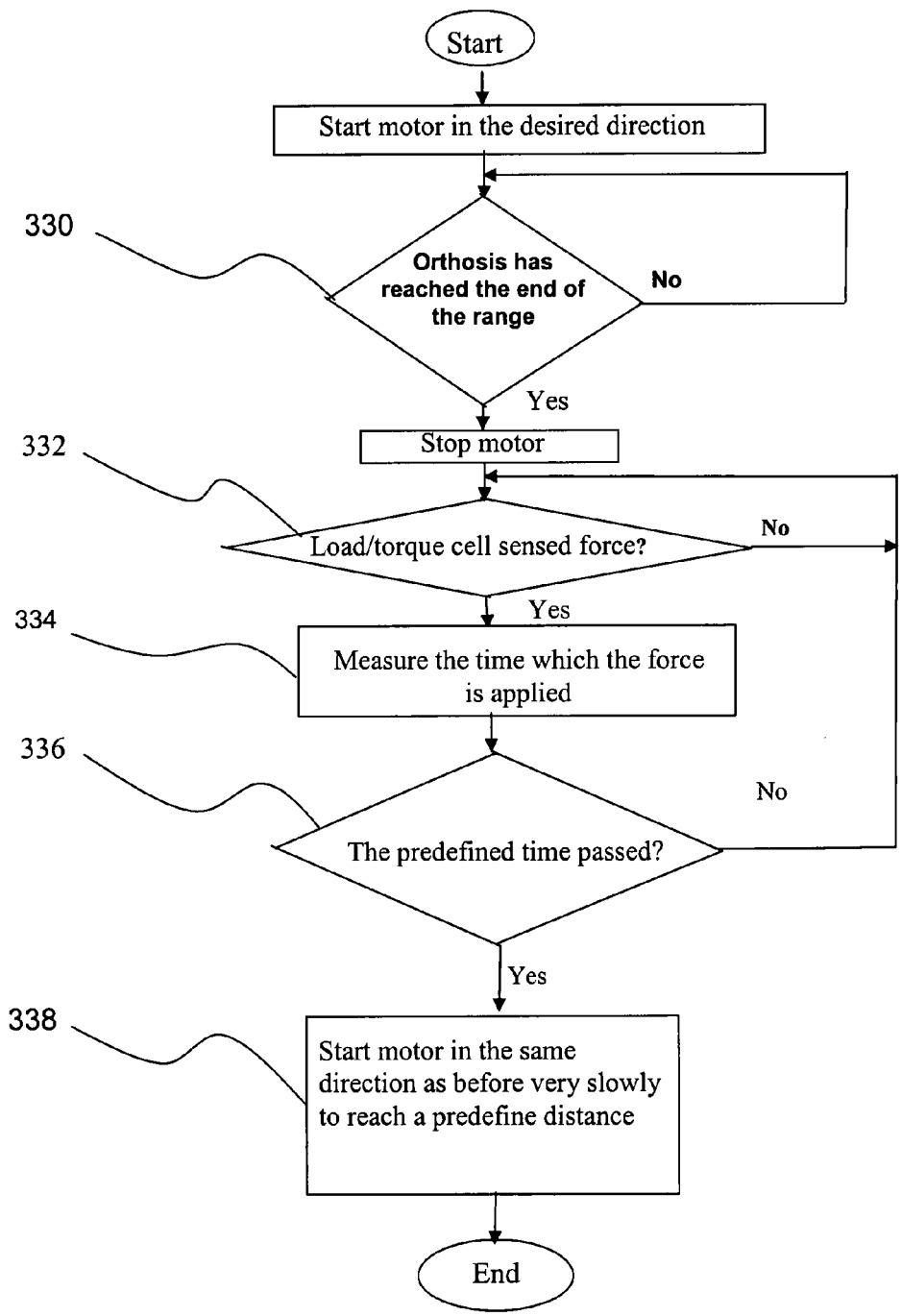
FIG. 25 shows a flow chart of a relax and hold technique treatment regimen according to the teachings of the present invention.
Figure 26:
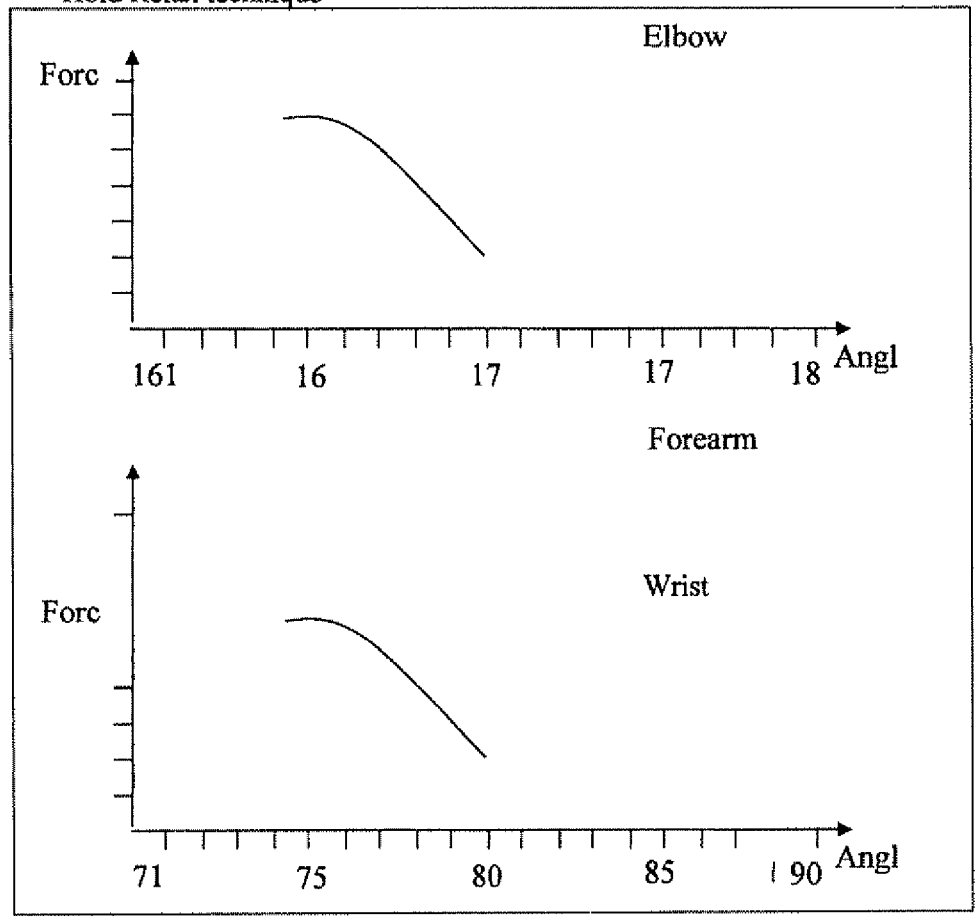
FIG. 26 shows a graphic representation of data collect during a relax and hold technique exercise treatment session according to the teachings of the present invention.
Figure 27:
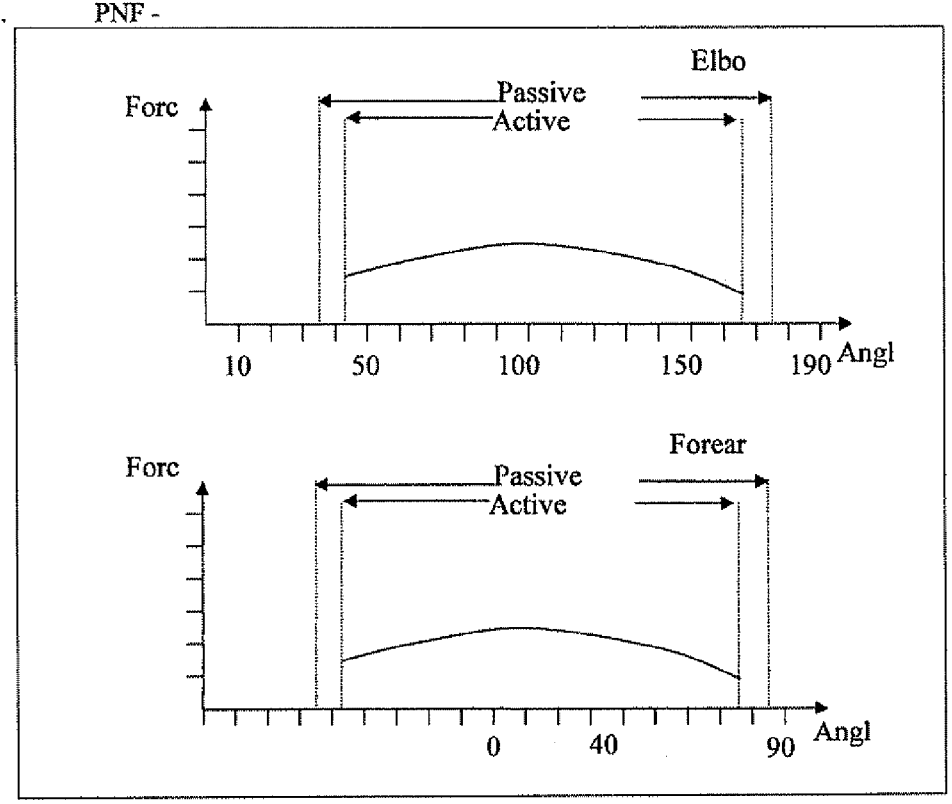
FIG. 27 shows a graphic representation of data collect during a PNF exercise treatment session according to the teachings of the present invention.

The 'hold' and 'relax' exercises may be used to increase either the active or passive range of motion or both. FIG. 25 presents in a non-limiting manner a flowchart of a 'hold' and 'relax' exercises used to extend the active range of motion according to the teaching of the present invention. The 'hold' and 'relax' exercises consist of bringing the external actuating device to a predefined border of a range of motion 330, then applying force and or movement beyond the border for short predefined periods of time for a specified number of repetitions. When working in the active range, the force in supplied by the patient. In the passive range, the force is supplied by the external actuating device. The external actuating device is advanced to a boundary of the active range of motion and advancement is stopped 330. The patient is instructed to move the arm so as to rotate the, for example, elbow joint beyond the boundary and the amount 332 of and length of time 334 force is applied is monitored. After a predefined length of time 336, the external actuating device is slowly advanced beyond the range of motion boundary for a predefined distance 338, for example 5°. All of the data from the session is saved 339, and may be added to the patient's treatment/assessment database examples of data that may be displayed for a hold and relax exercise is shown in FIG. 26, where force 340 is shown as a function of the angle 342, and data for the elbow 344 and forearm 346 are displayed individually.

PNF exercises are a type of static stretch most commonly characterized by a pre-contraction of the muscle to be stretched and a contraction of the antagonist muscle during the stretch. A PNF exercise according to the teaching of the present invention may be continuous motion of both the elbow and the forearm throughout a predefined range of motion at a predefined velocity, which may or may not vary during the exercise, for a predefined period of time. Rotation about the elbow and forearm axes of rotation during the treatment session may be sequential or simultaneous or a combination of the two. Illustrative, non-limiting examples of data that may be displayed are given in FIG. 27, where, the force is shown as a function of the angle.

The orthotic system of the present invention may be configured for clinical use whereby all of the elements of the system are located in the clinic. Alternatively, the external actuating device 2 and the remote control unit 500 may be supplied with computer software for remote communication to the clinic computer, whereby they will be configured for attachment to a home computer. In such a situation, real time control of the device will be monitored by the home computer, or on-board microprocessor and data will be transferred to the clinic computer via internet, or by direct telephone connection, for review by a doctor or therapist, at which time operational parameters may be reset to new values. A further alternative may circumvent the home computer and provide for direct connection to the clinic computer via telephone lines. In such a case, all of the operational parameters of the device would be controlled by the clinic computer, as would data collection and analysis. That is, the external actuating device will need to be plugged in to a telephone jack during treatment sessions.

It will be appreciated by one of ordinary skill in the art that the operational features, and data collection and analysis capabilities of an orthotic system according to the teachings of the present invention may be readily adapted for use in an assistive orthotic device. Such an assistive system may include a microchip to control real time operational parameters of the device, and supply a data link for connection to a computer for parameter review and adjustment. The remote control unit may be configured so as to be worn by the patient. Alternatively, the hydraulic system may be configured such that the external actuating device is self-contained. The operational regimen described above with regard to active range of motion assessment mode may be one non-limiting example of an assistive operational regimen for an orthotic system constructed and operative according to the principles of the present invention.

It will be appreciated that the above descriptions are intended only to serve as examples and that many other embodiments are possible within the spirit and the scope of the present invention.

Multi jointed orthosis with more that 2 joints and 3 actuators. The said disclosed invention is in effect an exoskeleton orthotic device and a method of its operation thereof. The disclosed exoskeleton device designed to be fitted and worn as external frame on a living not paralyzed limb. The axels of the so called "frame" are placed paralleled to the natural axels of the limb, thus, allowing the limb to move the said exoskeleton frame using its own muscles to rotate it around it natural axels under the limitations of the power that the said muscles can produce, and/or to let the exoskeleton frame rotate the living limb around its natural axels by use of actuators computer and/or processor memory driven programmed to fit medically to the limitations of the said limb and rotate it or rehabilitate it with out harming it. This demonstration by verbal explanation and figures emphases the said technology and invented control method as a logical solution for rotating body parts around their natural axis by their functioning plains as design by nature.

The disclosed method of actuating and control is actually a modification of the U.S. patent application Ser. No. 10/466,808. The said quoted patented orthodynamic rehabilitator is in effect an elbow device modified as the elbow sub component of the presently disclosed invention that had been described in detail; most relevant parts the abstract of the said patent has been engaged as main abstract of the disclosed invention, and is the main guide line to the actuating method and control of each subsystem of the disclosed invention as a suppurated unit, or if it was implemented as a component in a deferent device. However, when all the said subsystems tie together to form the said invention they need more innovative steps to allow them to perform in relation to each other and in true proportion to the human body which it is tied on. Thus, an explanation is required describing the connection method and control of the plains of operation of each subcomponent in regards to the axis tying each subcomponent to the others, as each one of the said axis capable of working only on one plain and has at list one actuator, at list one axel and at list two sensors.

One of the said sensors would be an Encoder that is capable of recording the radial angle of the plain in regards to other plain attached to it. One of the said sensors would be a Torque cell that is capable of recording the radial force exerted on the plain in regards to other plain attached to it.

One of the said sensors would be a load cell that is capable of recording the power exerted on the plain in regards to other plain attached to it. The said sensors electronic data transmitted by wire to the electronic board 102 to a connected processor 101, the data is converted to digital information as illustrated on FIG. 14 and transmitted by wire to the computer program, recorded and memorized. The program transmit operation orders as illustrated on FIG. 15 to the various actuators that actuate the relevant subsystem on its own plain of rotation in accordance to the pre assessed and memorized gap between the users limb active range of motion and his/hers passive range of motion. The assessment procedure is illustrated on FIG. 17.

In effect each subsystem rotates around its own axis on an entirely different plain. The work of each subsystem around its axis on its plain is carried on as follows: The wrist holder ring rotates the hand right and left as illustrates on FIG. 17 in a plain perpendicular to the hand, the said wrist holder ring actuate the tied in hand to perform 'Pronation' and/or 'Supination' as required by rotational actuator 50 assembled underneath on the said wrist holder 8 and moving it with gear 56 engaged to the holders gear 56a the said mechanism is illustrated in proportion on FIG. 4 and FIG. 9 The said wrist holder ring includes a clipper device 81 82 connected to it own small actuator that is designed to hold the Thumb and the Index finger in place, to assist the hand to grab and pick up things. The said clipper works on its own plain that is parallel to the fingers and perpendicular to the wrist holder ring.

Figure 30A:
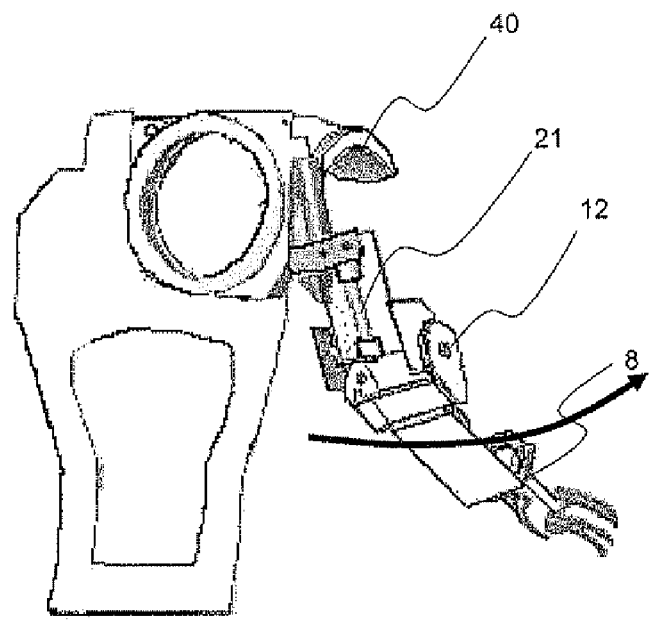
Figure 30B:
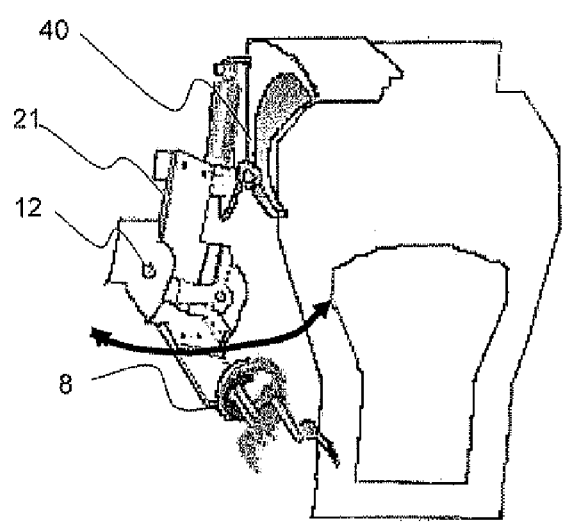

The forearm 10 which is a part of the elbow sub system rotates by an actuator 20 placed on the arm 4 and elbow gear 56 around the elbow axis 12 on a plain parallel to the forearm allowing rotation from 10 degrees to 135 degrees. The said actions are demonstrated on FIG. 8 The arm chassis is hung by an axel 21 that allows the elbow subsystem to rotate 45 degrees right and/or left on a plain horizontal to the vertical actuation plain of the elbow parts around their axis as illustrated on FIG. 30 The shoulder subsystem composed in effect of 3 more axels to allow it to function in parallel to the complex design of nature.

The said arm rotation axel 21 is hung from the shoulder mechanism body by a hinge supported axel 45 in a manner illustrated by FIG. 45 that provides partial capability of the natural shoulder axel (Glanoid) to allow the arm to swing by its actuating motor up to 90 degrees on a plain parallel to the human body.

Figure 2:
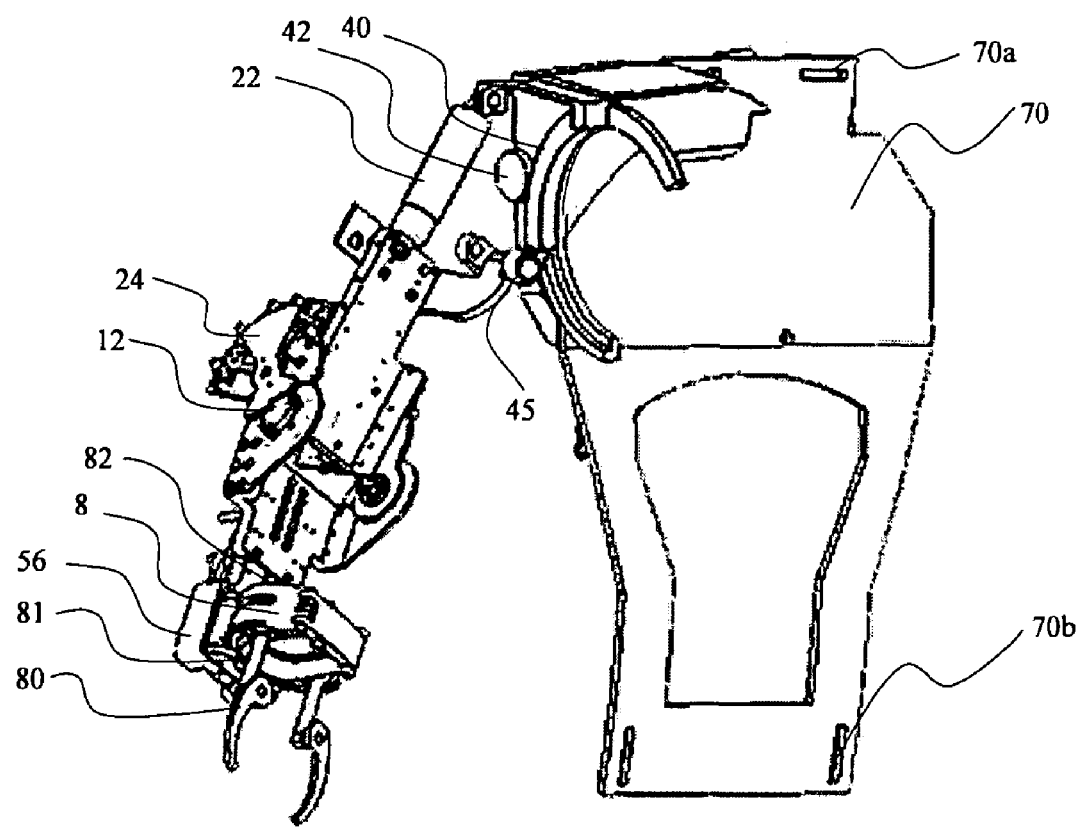
FIG. 2 shows a general drawing and front view of the disclosed invention operative according to the principles described in the following chapters in farther details.
Figure 31A:
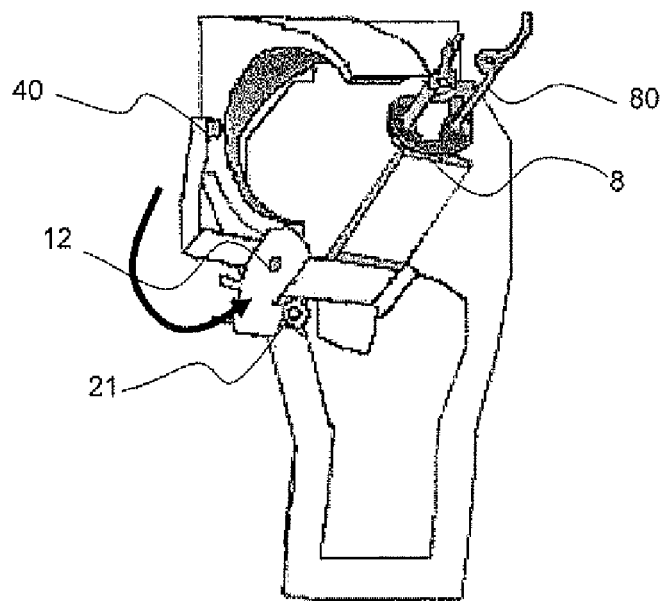
Figure 31B:
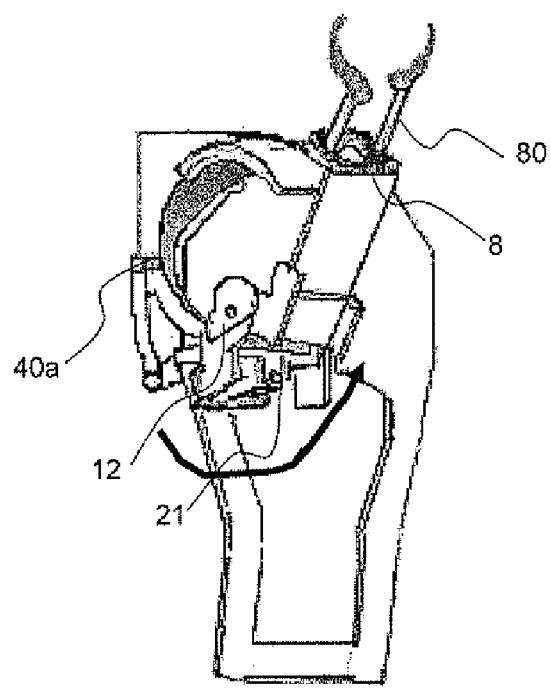

The said rotation on axel 45 could be continued; when the arm reaches 90 degrees the joint locks and yet another shoulder joint 43 takes it functioning role and provides the arm with another extension of 45 degrees on the same plain to prolong the limb range of motion as much as possible within the natural limitations of the user, as illustrated on said FIG. 33. Another axel 40 is involved in providing rotational capabilities to the arm by actuating motor 41 and a gear 42 operating on a half crassest toothed surface 43 on a plain vertical to the human body as illustrated on FIG. 31 and FIG. 32 sections a, b, and c. The said illustrations on the mentioned figures provide true scope of each subsystem axis and rotational plain and the mechanical relationship to its neighborly connected subsystems. All the said connected subsystems composing provides the description the said fully assembled exoskeleton device illustrated on FIG. 2 and FIG. 3 that in effect is capable of rotating by use of power, and/or react to human force by power simultaneously, parallel to the natural movement plains of the human limb on x, y, z axel dimensions. The sad motions are controlled by either by an external computer as illustrated on FIG. 14 or memory/processor imbedded on the arm chassis, in effect all the actuators and control systems are imbedded in the Orthosis and illustrated on FIG. 5 such as: Hydraulic Selector 3 and Hydraulic pump 3a motored by actuator 3b Main M board 101 and processor 102. The source of electric power could be direct AC converted to DC for use in home clinics and hospital or portable batteries carried on the user's belt. The said device is assembled on a light strong frame illustrated on FIG. 12 that allows attachments of left or right devices and/or both simultaneously. The frame designed to be tied to the user's body with shoulder crossed straps and waist Crosse straps pretty much like hikers back pack. The said type of frame designed to enable the user to wear on the device with simple aid of non qualified helper such as family member or friend. This type of frame could be worn on the body under or over the clothing, especially for use in home or outside for assisting the user on his/her ADL needs. It should be emphasized that implementation the of the assisting mode enables the user to use this invention for assistance only, to amplify in controlled and medically allowed manner the range of motion and the power of lifting of permanently partial impaired users.

The invention claimed is:

1. A method for self-adaptive motion treatment of a jointed body part of a patient, said jointed body part having at least three rotatable body sections interconnected by at least two joints, the method comprising:
   a) obtaining an exoskeleton multi-joint orthotic system having more than 2 joints, at least one is a shoulder joint and 3 external actuating devices;
   b) attaching said external actuating device physically to said jointed body part, said device including at least one actuator for applying force to generate or oppose movement of said jointed body part; at least one sensor arrangement for sensing a force generated by said jointed body part relative to said external actuating device; and, at least one sensor arrangement for sensing a position of said jointed body part; such that a first axis of device-rotation, which is an axis about which said body sections rotate in relation to each other, is placed upon a first axis of body-part-rotation; and at least a second axis of device-rotation is placed upon at least a second axis of body-part-rotation;
   c) activating said external actuating device during repeated performance of a set of motions including rotating the body sections about said axes of device-rotation so as to interact with said jointed body part according to a certain set of treatment parameters;
   d) during repetitions of said set of motions, collecting and storing data relating to the force generated by said jointed body part relative to said external actuating device and to the position of the jointed body part;
   e) analyzing said data by use of a data processor according to a predefined set of analysis rules; and,
   f) during said activating, modifying, responsive to said data analysis, at least one parameter of said set of treatment parameters during an uninterrupted treatment session, thereby modifying the interaction of said external actuating device with said jointed body part during at least one repetition of said set of motions based at least in part on data collected during previous repetitions of said set of motions.

2. The method of claim 1, wherein said rotating of said sections about said axis of device-rotation is implemented as rotation about said first and second axes of device-rotation, and said first and second axes of device-rotation are perpendicular to each other.

3. The method of claim 1, wherein said rotating about said first and second axes of device-rotation is implemented as substantially simultaneous rotation about said first and second axes of device-rotation.

4. The method of claim 1, wherein said activating further includes using a control unit in electronic communication with said data processor, said control unit further being in control communication with said external actuating device.

5. The method of claim 1, further comprising activating hydraulic actuators associated with said external actuating device to achieve said rotation, said control communication therefore being fluid communication.

6. The method of claim 1, wherein said certain set of treatment parameters relate to said activating being in a rehabilitative mode.

7. The method of claim 1, wherein said certain set of treatment parameters related to said activating device being in an assistive mode.

8. The method of claim 1, wherein said analysis is included in a decision making process of a treatment team.

9. A system for treating self-adaptive motion of a jointed body part of a patient, said jointed body part having at least three rotatable body sections interconnected by at least two joints, the system comprising:
   a) an exoskeleton multi-joint wear orthotic system having more than 2 joints, at least one is a shoulder joint and 3 external actuating devices;
   b) means for attaching said external actuating device physically to said jointed body part, said device including at least one actuator for applying force to generate or oppose movement of said jointed body part; at least one sensor arrangement for sensing a force generated by said jointed body part relative to said external actuating device; and, at least one sensor arrangement for sensing a position of said jointed body part; such that a first axis of device-rotation, which is an axis about which said body sections rotate in relation to each other, is placed upon a first axis of body-part-rotation; and at least a second axis of device-rotation is placed upon at least a second axis of body-part-rotation;
   c) means for activating said external actuating device during repeated performance of a set of motions including rotating the body parts about said axes of body-part-rotation so as to interact with said jointed body part according to a certain set of treatment parameters;
   d) means for repetitively collecting and storing data relating to the force generated by said jointed body part relative to said external actuating device and to the position of the jointed body part;
   e) means for analyzing said data by use of a data processor according to a predefined set of analysis rules; and,
   f) means for modifying, responsive to said data analysis, at least one parameter of said set of treatment parameters during activating an uninterrupted treatment session, thereby modifying the interaction of said external actuating device with said jointed body part during at least one repetition of said set of motions based at least in part on data collected during previous repetitions of said set of motions.

10. The system of claim 9, wherein said first and second axes of device-rotation are perpendicular to each other.

11. The system of claim 9, wherein said rotating about said two axes of device-rotation is implemented as substantially simultaneous rotation about said two axes of device-rotation.

12. The system of claim 9, wherein said data collection means include an encoder.

13. The system of claim 9, further comprising a control unit in electronic communication with said data processor, and in control communication with said external actuating device.

14. The system according to claim 13, further comprising hydraulic actuators associated with said external actuating device, said hydraulic actuators configured so as to rotate said sections about said axis device-rotation, said control communication therefore being fluid communication.

* * * * *